United States Patent
Zirpel et al.

(10) Patent No.: US 11,638,821 B2
(45) Date of Patent: May 2, 2023

(54) INCONTINENCE THERAPY

(71) Applicant: Medtronic, Inc., Minneapolis, MN (US)

(72) Inventors: Lance Zirpel, Lino Lakes, MN (US); Sudha B. Iyer, St. Paul, MN (US); Xuan K. Wei, Minnetonka, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 160 days.

(21) Appl. No.: 16/942,542

(22) Filed: Jul. 29, 2020

(65) Prior Publication Data

US 2021/0031032 A1 Feb. 4, 2021

Related U.S. Application Data

(60) Provisional application No. 62/972,904, filed on Feb. 11, 2020, provisional application No. 62/880,485, filed on Jul. 30, 2019.

(51) Int. Cl.
*A61N 1/36* (2006.01)

(52) U.S. Cl.
CPC ..... *A61N 1/36007* (2013.01); *A61N 1/36178* (2013.01)

(58) Field of Classification Search
CPC .......... A61N 1/36007; A61N 1/36178
See application file for complete search history.

(56) References Cited

U.S. PATENT DOCUMENTS

| | | |
|---|---|---|
| 8,989,861 B2 | 3/2015 | Su et al. |
| 9,089,699 B2 | 7/2015 | Su et al. |
| 9,168,374 B2 | 10/2015 | Su |
| 9,409,020 B2 | 8/2016 | Parker |
| 9,724,509 B2 | 8/2017 | Su et al. |
| 10,149,978 B1 | 12/2018 | Park |

(Continued)

FOREIGN PATENT DOCUMENTS

| | | |
|---|---|---|
| WO | 2011/156288 A1 | 12/2011 |
| WO | 2014/197564 A1 | 12/2014 |

(Continued)

OTHER PUBLICATIONS

International Search Report and Written Opinion of International Application No. PCT/US2020/044281, dated Nov. 6, 2020, 18 pp.

(Continued)

*Primary Examiner* — Amanda K Hulbert
(74) *Attorney, Agent, or Firm* — Shumaker & Sieffert, P.A.

(57) ABSTRACT

The disclosure describes example of subsensory electrical stimulation for providing therapy for incontinence. An implantable medical device (IMD) includes a memory configured to store a set of therapy parameters for subsensory electrical stimulation of a patient. The delivery of the subsensory electrical stimulation results in a therapeutic effect for incontinence therapy at a stimulation intensity that is in range of approximately 50% to 80% of a stimulation intensity at a sensory threshold, and the patient does not perceive delivery of the subsensory electrical stimulation and perceives delivery of stimulation at the sensory threshold. The IMD also includes therapy delivery circuitry configured to deliver the subsensory electrical stimulation based on the stored set of therapy parameters, including cycling the delivery of the subsensory electrical stimulation between an on-cycle and an off-cycle.

23 Claims, 10 Drawing Sheets

(56) References Cited

U.S. PATENT DOCUMENTS

| | | |
|---|---|---|
| 10,518,086 B2 | 12/2019 | Su et al. |
| 10,576,282 B2 | 3/2020 | Doan et al. |
| 2007/0100388 A1 | 5/2007 | Gerber |
| 2009/0054950 A1 | 2/2009 | Stephens |
| 2013/0079841 A1 | 3/2013 | Su et al. |
| 2014/0277256 A1 | 9/2014 | Osorio |
| 2015/0032181 A1 | 1/2015 | Baynham et al. |
| 2015/0148878 A1 | 5/2015 | Yoo et al. |
| 2015/0217116 A1 | 8/2015 | Parramon et al. |
| 2015/0328454 A1 | 11/2015 | Lambert |
| 2016/0114167 A1 | 4/2016 | Jiang et al. |
| 2016/0339250 A1 | 11/2016 | Kaula et al. |
| 2017/0239470 A1 | 8/2017 | Wei et al. |
| 2017/0291031 A1 | 10/2017 | Lee |
| 2018/0035924 A1 | 2/2018 | Gunderson et al. |
| 2018/0056073 A1 | 3/2018 | Torgerson |
| 2018/0078769 A1 | 3/2018 | Dinsmoor et al. |
| 2018/0133484 A1 | 5/2018 | Dinsmoor et al. |
| 2018/0369592 A1 | 12/2018 | Johanek |
| 2019/0001135 A1 | 1/2019 | Yoo et al. |
| 2019/0009098 A1 | 1/2019 | Jiang et al. |
| 2019/0046800 A1 | 2/2019 | Doan et al. |
| 2019/0060647 A1 | 2/2019 | Su et al. |
| 2019/0184168 A1 | 6/2019 | Vansickle et al. |
| 2019/0269924 A1 | 9/2019 | Su et al. |
| 2020/0078594 A1 | 3/2020 | Jiang et al. |
| 2021/0031033 A1 | 2/2021 | Davies et al. |
| 2021/0031041 A1 | 2/2021 | Davies et al. |
| 2021/0031042 A1 | 2/2021 | Davies et al. |

FOREIGN PATENT DOCUMENTS

| | | |
|---|---|---|
| WO | 2017/106539 A1 | 6/2017 |
| WO | 2018/080753 A1 | 5/2018 |
| WO | 2018/089418 A1 | 5/2018 |

OTHER PUBLICATIONS

"Guideline on Adjustment for Baseline Covariates in Clinical Trials," European Medicines Agency, Feb. 26, 2015, 11 pp.

"InterStim® Therapy N'Vision® Model 8840 Clinician Programmer and Model 8870 Application Card Programming Guide for Software Version B May 2008 supporting InterStim® II Model 3058 and InterStim® Model 3023 Neurostimulators," by Medtronic, M220804A004, May 2008, 160 pp.

"InterStim® Therapy, InterStim® II Model 3058 Neurostimulator, InterStim® Model 3023 Neurostimulator, Implant manual," by Medtronic, MA12231A010, May 2012, 32 pp.

"InterStim® Therapy, Programming Pointers, N'Vision® Clinician Programmer," by Medtronic, UC200604277 EN NI7249, 2006, 150 pp. (Applicant points out, in accordance with MPEP 609.04(a), that the year of publication, 2006, is sufficiently earlier than the effective U.S. filing date, so that the particular month of publication is not in issue.).

Altomare et al., "The Effects of Sacral Nerve Stimulation on Continence are Temporarily Maintained After Turning the Stimulator Off," Coloretcal Disease, vol. 15, No. 12, Dec. 2013, 8 pp.

Amend et al., "How Does Sacral Modulation Work Best? Placement and Programming Techniques to Maximize Efficacy," Current Urology Reports, vol. 12, No. 5, Oct. 2011, 9 pp.

Amundsen et al., "Sacral Neuromodulation for Intractable Urge Incontinence: Are There Factors Associated With Cure?," Adult Urology, vol. 66, No. 4, Oct. 2005, 5 pp.

Beer et al., "Cycling Versus Continuous Mode in Neuromodulator Programming: A Crossover Randomized Control Trial," Urologic Nursing, Vo. 36, No. 3, May-Jun. 2016, 16 pp.

Burton et al., "Effectiveness of Percutaneous Posterior Tibial Nerve Stimulation for Overactive Bladder: A Systematic Review and Meta-Analysis," Neurourology and Urodynamics, vol. 31, No. 8, Nov. 2012, 11 pp.

Cadish et al., "Stimulation Latency and Comparison of Cycling Regimens in Women Using Sacral Neuromodulation," Neurourology and Urodynamics, vol. 36, No. 2, Feb. 1, 2016, 4 pp.

Elterman et al., "The Novel Axonics® Rechargeable Sacral Neuromodulation System: Procedural and Technical Impressions from an Initial North American Experience," Neurourology and Urodynamics, vol. 37, No. S2, Feb. 2018, 8 pp.

Hoen et al., "Intermittent Sacral Neuromodulation for Idiopathic Urgency Urinary Incontinence in Women," Neurourology and Urodynamics, vol. 36, No. 2, Feb. 2017, 5 pp.

Janknegt et al., "Improving Neuromodulation Technique for Refractory Voiding Dysfunctions: Two-Stage Implant," Adult Urology, vol. 49, No. 3, Mar. 1997, 5 pp.

Mahfooz et al., "Parameters of Successful Sacral Root Neuromodulation of the Pelvic Floor: a Retrospective Study," The Canadian Journal of Urology, vol. 11, No. 3, Jun. 2004, 8 pp.

Marcelissen et al., "The Effect of Pulse Rate Changes on the Clinical Outcome of Sacral Neuromodulation," The Journal of Urology, vol. 185, No. 5, May 2011, 5 pp.

Markle et al., "Prospective Randomized Crossover Trial Comparing Continuous and Cyclic Stimulation in InterStim Therapy," Female Pelvic Medicine & Reconstructive Surgery, vol. 21, No. 6, Nov.-Dec. 2015, 4 pp.

Maxwell et al., "Reprogramming Requirements After Sacral Nerve Stimulator Implantation: Correlation with Preoperative Indication," The Journal of Urology, vol. 179, No. 2, Feb. 2008, 3 pp.

Michelsen et al., "A Prospective, Randomized Study: Switch Off The Sacral Nerve Stimulator During the Night?," Diseases of the Colon and Rectum, vol. 51, No. 5, Jun. 2008, 3 pp.

Noblett et al., "Results of a Prospective, Multicenter Study Evaluating Quality of Life, Safety, and Efficacy of Sacral Neuromodulation at Twelve Months in Subjects with Symptoms of Overactive Bladder," Neurourology and Urodynamics, vol. 35, No. 2, Feb. 2016, 6 pp.

Oerlemans et al., "Is on-Demand Sacral Neuromodulation in Patients With OAB Syndrome a Feasible Therapy Regime?", Neurourology and Urodynamics, vol. 30, No. 8, Nov. 2011, 4 pp.

Peters et al., "Effect of Sacral Neuromodulation Rate on Overactive Bladder Symptoms: A Randomized Crossover Feasibility Study," Lower Urinary Tract Symptoms, vol. vol. 5, No. 3, Sep. 2013, 5 pp.

Peters et al., "Randomized Trial of Percutaneous Tibial Nerve Stimulation Versus Sham Efficacy in the Treatment of Overactive Bladder Syndrome: Results from the SUmiT Trial," The Journal of Urology, vol. 183, No. 4, Apr. 2010, 6 pp.

Peters et al., "The Relationship Between Subjective and Objective Assessments of Sacral Neuromodulation Effectiveness in Patients with Urgency-Frequency," Neurourology and Urodynamics, vol. 27, No. 8, Nov. 2008, 4 pp.

Price et al., "Prospective Randomized Crossover Trial Comparing Continuous and Cyclic Stimulation in InterStim Therapy", Female Pelvic Medicine & Reconstructive Surgery, vol. 21, No. 6, Nov./Dec. 2015, 4 pp.

Scheepens et al., "Predictive Factors for Sacral Neuromodulation in Chronic Lower Urinary Tract Dysfunction," Adult Urology, vol. 60, No. 4. Oct. 2002, 5 pp.

Schmidt et al., "Sacral Nerve Stimulation for Treatment of Refractory Urinary Urge Incontinence," The Journal of Urology, vol. 162, No. 2, Aug. 1999, 6 pp.

Siegel et al., "Long-Term Results of a Multicenter Study on Sacral Nerve Stimulation for Treatment of Urinary Urge Incontinence, Urgency-Frequency, and Retention," Urology, vol. 56, No. 6, Supp. 1, Dec. 2000, 5 pp.

Siegel et al., "Prospective Randomized Feasibility Study Assessing the Effect of Cyclic Sacral Neuromodulation on Urinary Urge Incontinence in Women," Female Pelvic Medicine & Reconstructive Surgery, vol. 00, No. 00, Mar. 2017, 5 pp.

Snellings et al., "Effects of Stimulation Site and Stimulation Parameters on Bladder Inhibition by Electrical Nerve Stimulation," BJU International, vol. 110, No. 1, Jul. 2012, 8 pp.

Su et al., "Electromyographic Response Across Different Pulse-Widths of Sacral Neuromodulation in Sleep," Neuromodution: Technology at the Neural Interface, vol. 22, No. 6, Feb. 2018, 6 pp.

(56) References Cited

OTHER PUBLICATIONS

Su et al., "Neuromodulation in a Rat Model of the Bladder Micturition Reflex," American Journal of Physiology, vol. 302, No. 4, Feb. 15, 2012, 10 pp.

Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21, No. 1, Jan. 2018, 10 pp.

Van Der Pal et al., "Percutaneous tibial nerve stimulation in the treatment of refractory overactive bladder syndrome: is maintenance treatment necessary?," BJU International, vol. 97, No. 3, Mar. 2006, 4 pp.

Worsoe et al., "Turning Off Sacral Nerve Stimulation Does Not Affect Gastric and Small Intestinal Motility in Patients Treated for Faecal Incontinence," Colorectal Disease, vol. 14, No. 10, Oct. 2012, 8 pp.

Zhang et al., "Neural Pathways Involved in Sacral Neuromodulation of Reflex Bladder Activity in Cats," American Journal of Physiology, Renal Physiology, vol. 304, No. 6, Mar. 2013, 8 pp.

U.S. Appl. No. 16/797,065, filed Feb. 21, 2020, naming inventors Davies et al.

International Preliminary Report on Patentability from International Application No. PCT/US2020/044281, dated Feb. 10, 2022, 11 pp.

INCONTINENCE THERAPY

This application claims the benefit of U.S. Provisional Application No. 62/880,485, filed Jul. 30, 2019, and U.S. Provisional Application No. 62/972,904, filed Feb. 11, 2020, the entire content of each of which is hereby incorporated by reference.

TECHNICAL FIELD

The disclosure relates to medical devices and, more particularly, to medical devices configured to deliver electrical stimulation therapy.

BACKGROUND

Urinary incontinence, or an inability to control urinary function, is a problem that afflicts people of all ages, genders, and races. Various muscles, nerves, organs, and conduits within the pelvic floor cooperate to collect, store, and release urine. A variety of disorders may compromise a patient's urinary tract performance and contribute to incontinence. Many such disorders may be associated with aging, injury, or illness.

Urinary incontinence, or degree of urgency associated with incontinence, may originate from disorders of portions of the peripheral or central nervous system which control the bladder micturition reflex. Nerve disorders may also lead to overactive bladder activities and/or may prevent proper triggering and operation of the bladder. Furthermore, urinary incontinence may also result from improper communication between the nervous system and the bladder.

SUMMARY

Devices, systems, and techniques for managing incontinence (bladder incontinence and/or fecal incontinence) of a patient and/or other patient conditions using electrical stimulation are described in this disclosure. In some examples, processing circuitry may be configured to determine a sensory threshold. A sensory threshold may refer to a minimum electrical stimulation intensity (e.g., electrical stimulation level) at or above which a particular physiological response to electrical stimulation occurs, and below which (i.e., if the electrical stimulation intensity is reduced) the particular physiological response no longer occurs. For example, the sensory threshold is the minimum electrical stimulation intensity at or above which the patient perceives the stimulation, and below which (i.e., if the electrical stimulation intensity is reduced) the patient does not perceive the stimulation. In one or more examples, the processing circuitry may be configured to cause therapy delivery with subsensory electrical stimulation (i.e., with an electrical stimulation intensity that is less than the sensory threshold). As one example, a stimulation intensity of the subsensory electrical stimulation is 90% to 10% of a stimulation intensity at the sensory threshold (e.g., 50% or less than the stimulation intensity at the sensory threshold). The stimulation intensity of the subsensory electrical stimulation may be 80% to 50% of the stimulation intensity at the sensory threshold. The stimulation intensity may be based on a combination of various stimulation parameters such as amplitude, pulse width, and frequency and can be controlled by one or more of these parameters.

In accordance with techniques described in this disclosure, even when electrical stimulation is delivered at subsensory level, the patient may still experience efficacious therapy for incontinence. For example, electrical stimulation may be subsensory in the sense that the electrical stimulation intensity is insufficient to cause an acute physiological response, such as a motor response, patient perception response, or a detected physiological effect, during stimulation. However, the patient may still experience therapeutic effect even if the electrical stimulation is insufficient to cause an acute physiological response. As an example, the patient may receive subsensory electrical stimulation to at least one of a sacral nerve or tibial nerve to provide immediate therapeutic effect caused by the ongoing delivery of the subsensory electrical stimulation to address incontinence. As described above, a stimulation intensity of the subsensory electrical stimulation may be in range of approximately 50% to less than 80% of a stimulation intensity at a sensory threshold, and the patient may not perceive delivery of the subsensory electrical stimulation.

By delivering electrical stimulation at a subsensory level, an implantable medical device (IMD) may consume less power delivering therapy as compared to delivering electrical stimulation at or greater than the sensory threshold. Accordingly, this disclosure describes example techniques that may increase operational longevity of the IMD (e.g., before the IMD needs to be recharged or replaced) with minimal to no impact on therapy efficacy. In this way, the example techniques of delivering electrical stimulation at the subsensory level may reduce power consumption and thereby increase longevity of primary cell devices (e.g., IMDs that include non-rechargeable power sources), or increase recharge intervals for rechargeable devices (e.g., IMDs that include rechargeable power sources), while also reducing unwanted or unpleasant sensations from the electrical stimulation.

In one example, the disclosure describes a system comprising a memory configured to store a first set of therapy parameters for delivery of sensory electrical stimulation at a sensory threshold during a therapy induction phase and a second set of therapy parameters for delivery of subsensory electrical stimulation during a therapy maintenance phase and therapy delivery circuitry configured to continuously deliver the sensory electrical stimulation at the sensory threshold to a patient based on the first set of therapy parameters during the therapy induction phase, wherein delivery of the sensory electrical stimulation at the sensory threshold results in a therapeutic effect for incontinence therapy, wherein the therapy induction phase includes at least four weeks after implantation of an implantable medical device (IMD) within the patient, and wherein the patient perceives delivery of the sensory electrical stimulation at the sensory threshold, and cycle delivery of the subsensory electrical stimulation to the patient, between an on-cycle and an off-cycle, according to a cycle ratio of between about 2% and 50%, based on the second set of therapy parameters during the therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

In one example, the disclosure describes a method comprising continuously delivering, with an implantable medical device (IMD), sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold, and cycling, with the IMD, delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

In one example, the disclosure describes a computer-readable storage medium storing instructions thereon that when executed cause one or more processors of an implantable medical device (IMD) to continuously deliver sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold, and cycle delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

In one example, the disclosure describes an implantable medical device (IMD) comprising a memory configured to store a set of therapy parameters for subsensory electrical stimulation of a patient and therapy delivery circuitry configured to deliver the subsensory electrical stimulation to at least one of a sacral nerve or tibial nerve based on the stored set of therapy parameters to provide immediate therapeutic effect caused by the ongoing delivery of the subsensory electrical stimulation to address incontinence, wherein a stimulation intensity of the subsensory electrical stimulation is less than 80% of a stimulation intensity at a sensory threshold, and wherein the patient does not perceive delivery of the subsensory electrical stimulation and perceives delivery of stimulation at the sensory threshold.

The details of one or more aspects of the disclosure are set forth in the accompanying drawings and the description below.

Figure 1:
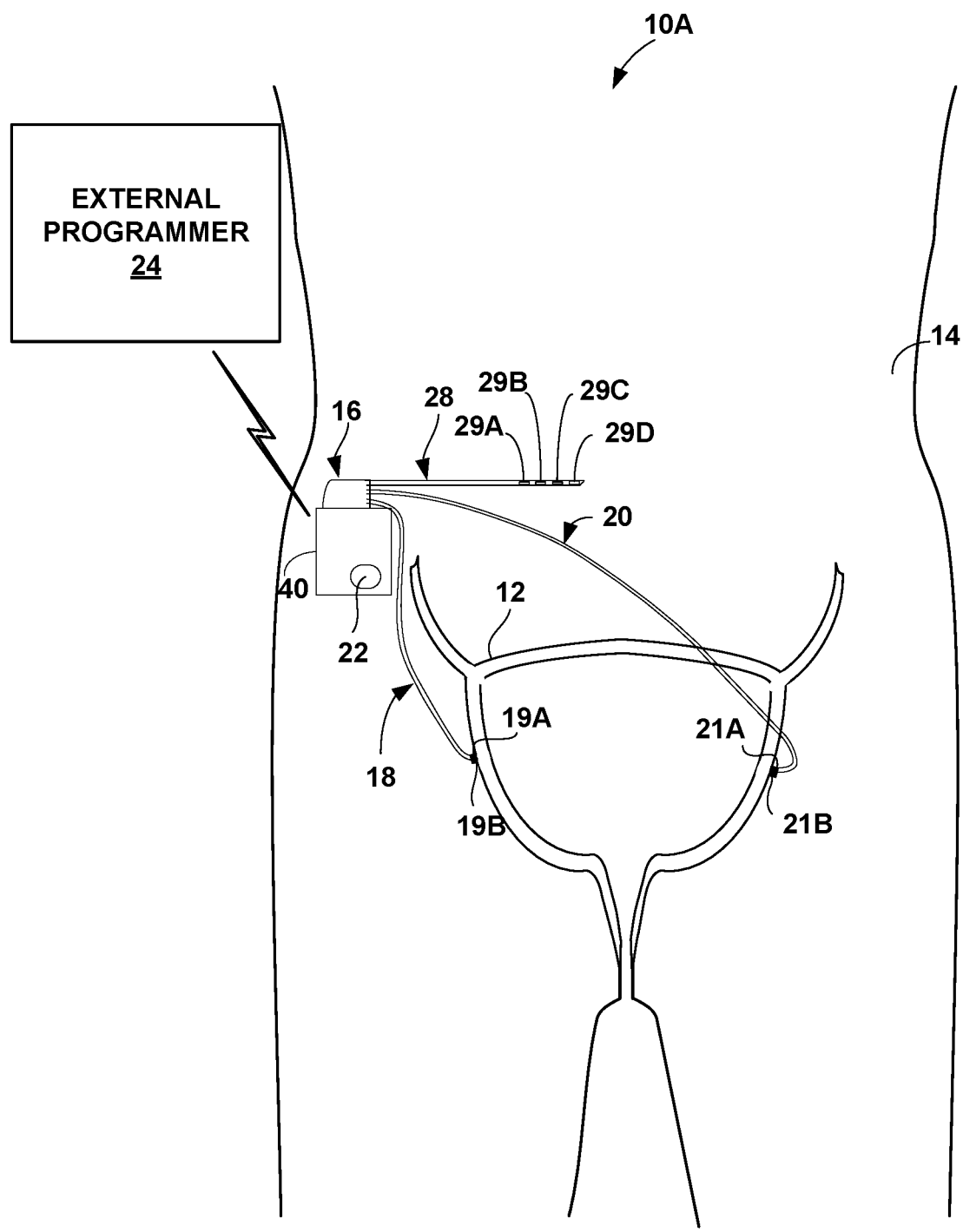
FIG. 1 illustrates, diagrammatically, a patient with an example implanted medical device including a therapy delivery circuitry.

The details of one or more examples of this disclosure are set forth in the accompanying drawings and the description below. Other features, objects, and advantages of this disclosure will be apparent from the description and drawings, and from the claims.

DETAILED DESCRIPTION

As described above, devices, systems, and techniques for managing incontinence (e.g., urinary incontinence and/or fecal incontinence) of a patient and/or other patient conditions using electrical stimulation are described in this disclosure. In some examples, a medical device is configured to deliver electrical stimulation at subsensory levels.

In general, a sensory threshold may be a perception threshold. When electrical stimulation is delivered at or above the perception threshold, the patient is able to perceive the electrical stimulation (e.g., feel the stimulation). In this example, subsensory electrical stimulation (e.g., sub-perception stimulation) may refer to a level of electrical stimulation that is delivered to the patient but at which the patient does not perceive (e.g., feel) the electrical stimulation.

There may be various other examples of perception threshold and the patient perceiving or not perceiving the stimulation. As one example, the patient perceiving the delivery of stimulation at the sensory threshold may be the patient responding with a motor response (e.g., muscle movement) to the stimulation at the sensory threshold. The patient not perceiving the delivery of subsensory electrical stimulation may be the patient not responding to the subsensory electrical stimulation with the motor response.

As another example, the patient perceiving the delivery of stimulation at the sensory threshold may be the patient generating a detected (e.g., detectable) electrical signal in response to the stimulation at the sensory threshold. One example of the electrical signal generated by the patient in response to an electrical stimulation greater than or equal to the sensory threshold is an electromyography (EMG) signal.

Another example of the electrical signal generated by the patient in response to an electrical stimulation greater than or equal to the sensory threshold is an evoked compound action potential (eCAP) such as a nerve action potential. An EMG signal and an eCAP are examples and should not be considered limiting. The patient not perceiving the delivery of stimulation may include the patient not generating the detected or detectable electrical signal (e.g., amplitude of eCAP or EMG signal is too small).

Accordingly, the sensory threshold may mean the delivery of electrical stimulation at the sensory threshold that results in some form of perception of the stimulation (e.g., feeling the stimulation, having a motor movement, etc.). Subsensory electrical stimulation may mean the delivery of electrical stimulation having a stimulation intensity that is less than the stimulation intensity of the stimulation at the sensory threshold. With subsensory electrical stimulation, the actual stimulation may result in therapeutic effect for the incontinence. However, the patient may not perceive the stimulation (e.g., not feel the stimulation, not have a motor movement, and/or not generate an electrical signal). In some examples, the stimulation intensity of the subsensory electrical stimulation may be less than or equal to 90% of the stimulation intensity at the sensory threshold (e.g., stimulation intensity of the electrical stimulation being delivered at the sensory threshold). For instance, the stimulation intensity of the subsensory electrical stimulation may be in a range of approximately 90% to 10% of the stimulation intensity at the sensory threshold, including examples where the stimulation intensity of the subsensory electrical stimulation is approximately 50% or less of the stimulation intensity at the sensory threshold. The stimulation intensity of the sub sensory electrical stimulation may be in a range of approximately 80% to 50% of the stimulation intensity at the sensory threshold.

The above describes various examples of a sensory threshold and subsensory electrical stimulation. For instance, the sensory threshold may include the patient feeling the stimulation, the patient having a motor response, etc. In some example, the sensory threshold may include the patient generating a detected or detectable electrical signal. The electrical stimulation intensity for each may all be different or two or more may be the same.

In accordance with one or more examples described in this disclosure, the parameters of the subsensory electrical stimulation may be selected such that the patient does not perceive the stimulation. The patient not perceiving the stimulation may mean one or more of the patient not feeling the stimulation, and having no motor response to the stimulation. For instance, in some cases, the patient may be considered as not perceiving the stimulation when the patient does not feel the stimulation, but it is still possible that there is a motor response (e.g., the patient may not feel the electrical stimulation but may feel the motor response to the electrical stimulation). In some cases, the patient may be considered as not perceiving the stimulation when the patient does not feel the stimulation but the patient generates an electrical signal. In some cases, the patient may be considered as not perceiving the stimulation when there is no motor response but the patient still feels the stimulation. Any such permutation or combination is possible.

In some examples, when a medical device delivers electrical stimulation at or above the sensory threshold, a particular physiological response occurs. For instance, when the medical device delivers electrical stimulation at a first level, the patient feels the electrical stimulation. When the medical device delivers electrical stimulation at a second level, the patient moves a muscle (e.g., has a motor response) but may or may not feel the stimulation but may still feel the motor response. When the medical device delivers electrical stimulation at a third level, the patient generates an electrical signal (e.g., EMG signal or eCAP) but may or may not feel the stimulation and may or may not have a motor response. The first, second, and third levels may be different or two or more may be the same. In some examples, a clinician or the medical device may determine one or more of the sensory thresholds, each of which is the minimal electrical simulation needed to cause the particular physiological response to occur.

As described in more detail, the disclosure describes example techniques of delivering subsensory electrical stimulation. For instance, the medical device may be configured to deliver electrical stimulation that is substantially below the sensory threshold. The intensity of the subsensory electrical stimulation may be less than all of the first level (e.g., feeling of stimulation), second level (e.g., motor response), and third level (e.g., EMG signal or eCAP). In some examples, the intensity of the subsensory electrical stimulation may be greater than one or more of the first level, the second level, or the third level but less than at least one of the first level, the second level, or the third level.

Substantially below the sensory threshold refers to electrical stimulation that is less than 90% of the sensory threshold. In other words, delivery of the subsensory electrical stimulation results in a therapeutic effect for incontinence therapy at a stimulation intensity that is less than or equal to approximately 90% of a stimulation intensity at a sensory threshold. The stimulation intensity of the subsensory electrical stimulation may include electrical stimulation having intensity that is less than approximately 80%, 70%, 60%, 50%, 40%, 30%, or 20% but greater than 0% of the stimulation intensity at the sensory threshold. In some examples, the intensity of the subsensory electrical stimulation may be approximately 80% to 50% of the stimulation intensity at the sensory threshold.

As described in more detail, subsensory electrical stimulation (and not a time when stimulation is not being delivered) may be effective for treating incontinence such as urinary incontinence and fecal incontinence. For example, the patient may receive subsensory electrical stimulation to provide immediate therapeutic effect caused by the ongoing delivery of the subsensory electrical stimulation to address incontinence, where a stimulation intensity of the subsensory electrical stimulation in range of approximately 50% to less than 80% of a stimulation intensity at a sensory threshold, and where the patient does not perceive delivery of the subsensory electrical stimulation and perceives delivery of stimulation at the sensory threshold. In this disclosure, "immediate therapeutic effect caused by the ongoing delivery of the subsensory electrical stimulation" refers to the subsensory electrical stimulation itself providing therapeutic effect rather than there being a delay in when the patient experiences therapeutic effect, such as where the therapeutic effect is after the subsensory electrical stimulation is turned off or even lower levels of subsensory electrical stimulation is applied. For instance, the patient may experience therapeutic effect while the subsensory electrical stimulation is being delivered (e.g., due to the ongoing delivery of the subsensory electrical stimulation).

In the above examples, the IMD delivers subsensory electrical stimulation to a patient. In some examples, the subsensory electrical stimulation may be continuous. However, in some examples, to further reduce battery drain, the IMD may be configured to cycle the delivery of subsensory electrical stimulation. Cycling delivery of subsensory electrical stimulation refers to cycling between an on-cycle and an off-cycle. In the on-cycle, the IMD is configured to deliver the subsensory electrical stimulation, and during the off-cycle, the IMD is configured to not deliver electrical stimulation (e.g., cease delivery of electrical stimulation). During the on-cycle, electrical stimulation may be actively delivered as pulses or bursts of pulses. Thus, although there may be a period of time during the on-cycle in which an electrical stimulation signal has an amplitude of about 0 (e.g., between pulses or bursts of pulses), the subsensory electrical stimulation signal may still be considered to be actively delivered during the on-cycle. During the off-cycle, the IMD is not actively delivering an electrical stimulation signal to the patient.

The on-cycle and the off-cycle may together define a cycle ratio. One example of the cycle ratio is the on-cycle divided by the result of the on-cycle plus the off-cycle (e.g., on-cycle/(on-cycle+off-cycle)). For example, if the on-cycle is 30 minutes and the off-cycle is 23.5 hours, then the cycle ratio is 2.08% (e.g., 30 minutes/(30 minutes+1410 minutes). If the on-cycle is 8 hours and the off-cycle is 16 hours, then the cycle ratio is 33% (e.g., 8/(8+16)). If the on-cycle is 1.5 hours and the off-cycle is 1.5 hours, then the cycle ratio is 50% (e.g., 1.5/(1.5+1.5)).

Accordingly, in one or more examples, the IMD may be configured to cycle delivery of the subsensory electrical stimulation to the patient, between an on-cycle and an off-cycle, according to a cycle ratio of between about 2% and 50%, including 33% and 50%. The subsensory electrical stimulation may have a stimulation intensity in range of less than 50% to approximately 80% of the stimulation intensity at the sensory threshold.

Urinary incontinence refers to a condition of involuntary loss of urine, and may include urge urinary incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence, disorders in which urination does not occur as desired, such as urinary retention disorder, and overactive bladder. Symptoms of overactive bladder may include one or more of urge incontinence, frequent urination, and urgency (frequent urges to urinate). While urinary incontinence is primarily referred to herein, the devices, systems, and techniques described herein may also be used to manage a fecal incontinence condition of a patient.

Electrical stimulation therapy may include delivery of electrical stimulation to one or more target tissue sites proximate to one or more peripheral nerves (e.g., the sacral, pudendal, dorsal nerve of the penis or clitoris, and tibial nerves, and branches thereof) via a medical device to modulate activity of the one or more peripheral nerves. Such electrical stimulation may be used to modify pelvic floor function to manage various patient conditions (e.g., urinary incontinence and fecal incontinence). Although the present disclosure describes the delivery of electrical stimulation therapy by an implantable medical device (IMD), the devices, systems, and techniques of the present disclosure also may be implemented by an external medical device that delivers electrical stimulation therapy via implanted or external electrodes.

Some medical device systems for delivering electrical stimulation therapy to a patient for the management of a urinary or fecal incontinence condition may be configured to deliver electrical stimulation therapy such that a patient responds to the electrical stimulation therapy. The patient responding to the electrical stimulation therapy includes examples where the patient perceives the electrical stimulation therapy (e.g., verbally or through some other way indicates that he or she can feel the therapy) and includes examples where the patient generates a visually perceivable or a recordable response (e.g., a muscle movement). In some examples, patient responding to the electrical stimulation therapy includes examples where the patient generates an electromyography (EMG) signal, even if the muscle movement is not visually perceivable, or generates an evoked compound action potential (eCAP). The EMG signal or the eCAP may be sensed by sensing circuitry of the IMD.

Techniques for delivering therapy where a patient responds to the electrical stimulation therapy are referred to as delivering sensory stimulation or stimulation at the sensory threshold. In other words, delivering sensory stimulation or stimulation at the sensory threshold means delivering electrical stimulation where a physiological response occurs (e.g., perception of therapy, motor response, or detectable electrical signal generation).

While delivering electrical stimulation at the sensory threshold provides efficacious treatment for incontinence, power savings may be achieved by delivering electrical stimulation at subsensory levels. For instance, the amount of power that the medical device consumes delivering electrical stimulation at or above the sensory threshold may be greater than the amount of power that the medical device consumes delivering electrical stimulation below the sensory threshold. By delivering electrical stimulation at subsensory levels, the life of the power source (e.g., battery, capacitor cell, etc.) of the medical device may be extended, compared to delivery of electrical stimulation at suprasensory levels. For instance, in examples where the power source is a primary cell (e.g., non-rechargeable), the life of the power source may be extended by delivering electrical stimulation at subsensory levels, thereby extending the life of the medical device and extending the time before surgery is needed to replace the medical device. In examples where the power source is a rechargeable cell, the life of the power source may be extended by delivering electrical stimulation at subsensory levels, thereby extending the amount of time before recharge is needed.

As described above, in some examples, to further extend battery life, the medical device may be configured to cycle delivery of the subsensory electrical stimulation to the patient. For example, the medical device may deliver subsensory electrical stimulation for an on-cycle, and then cease delivery of electrical stimulation for an off-cycle, followed by delivery of subsensory electrical stimulation for an on-cycle and so forth.

Conventionally, delivering electrical stimulation below the sensory threshold was not recognized as providing efficacious treatment. However, as described in more detail below, based on clinical data (as described in more detail with respect to FIG. 7 and FIG. 10), efficacious treatment for incontinence is still possible even when electrical stimulation is delivered at subsensory levels. For instance, the amount of electrical stimulation that is delivered is based on a plurality of stimulation parameters such as amplitude (e.g., voltage or current amplitude), pulse width, and frequency. In some conventional techniques, a medical device is configured to deliver electrical stimulation having a particular amplitude, pulse width, and frequency such that the electrical stimulation intensity is at or near the sensory threshold.

In accordance with techniques described in this disclosure, the medical device may be configured to deliver therapy at a lower amplitude, pulse width, and/or frequency such that the medical device is delivering subsensory electrical stimulation (e.g., stimulation at a subsensory level). Clinical data, generated by delivering subsensory electrical stimulation, showed that even when subsensory electrical stimulation is delivered, a patient may have limited to no incontinence episodes, or at least no more or few more incontinence episodes as compared to delivery of electrical stimulation at sensory threshold. In some cases, the stimulation intensity for the subsensory electrical stimulation may be in a range of 90% to 10% of the stimulation intensity at the sensory threshold, including at or less than 50%. As another example, the stimulation intensity for the subsensory electrical stimulation may be in a range of 80% to 50% of the stimulation intensity at the sensory threshold.

As one example, assume that the electrical parameters for electrical stimulation at the sensory threshold are 1 mA amplitude, 210 micro-second pulse width, and 14 Hz frequency. The pulse width may be in range of 60 micro-seconds to 210 micro-seconds, and the frequency may be in range of 5 Hz to 25 Hz, as a few non-limiting examples. In some examples, the patient may experience efficacious treatment if the amplitude were reduced from 1 mA by 20% to 50% (e.g., 0.8 mA to 0.5 mA, respectively) and the pulse width were reduced to 100 micro-seconds, with the frequency remaining at 14 Hz. In this example, the patient may not feel the electrical stimulation (e.g., no perception) or show a motor response to electrical stimulation but would still experience efficacious treatment from the delivery of the therapy (e.g., the delivery of therapy is causing the therapeutic effect).

In some examples, additional modifications to the treatment are possible. As one example, as described above, the medical device may deliver therapy through a plurality of cycle settings. For example, rather than providing continuous subsensory electrical stimulation, the medical device may deliver subsensory electrical stimulation for a first time period (e.g., on-cycle), and then no stimulation for a second time period (e.g., off-cycle), followed by subsensory electrical stimulation for a third time period (e.g., on-cycle), and so forth.

In the examples described herein, a medical device may deliver electrical stimulation therapy to treat one more patient conditions associated with the urinary bladder and associated portions of the nervous system. Although examples of the disclosure primarily are described with respect to managing patient conditions such as urge incontinence, urinary incontinence, or urine retention, the devices, systems, and techniques described herein may be configured to manage other patient conditions, such as overactive bowel, irritable bowel, pelvic pain, urgency frequency, bowel pain, bladder pain, and the like. For example, the devices, systems, and techniques described herein may be applied to the delivery of electrical stimulation to inhibit bowel contraction, e.g., in a manner that treats a bowel condition, such as fecal incontinence or irritable bowel syndrome. In any such examples, the patient may experience a reduction in the symptoms associated with the patient condition that the delivered electrical stimulation therapy is configured to manage.

FIG. 1 is a conceptual diagram illustrating an example therapy system 10A that delivers electrical stimulation therapy to a patient 14 to manage an urgency and/or urinary incontinence disorder of patient 14. Therapy system 10A is an example of a therapy system configured to implement the techniques described herein for delivering subsensory electrical stimulation therapy. Therapy system 10A includes an implantable medical device (IMD) 16, which is coupled to leads 18, 20, and 28, sensing circuitry 22, and external programmer 24. IMD 16 generally operates as a therapy device configured to generate and deliver electrical stimulation to, for example, a tissue site proximate a pelvic floor nerve, a pelvic floor muscle, the urinary sphincter, a detrusor muscle, or other pelvic floor targets. Pelvic floor nerves include peripheral nerves such as sacral nerves, pudendal nerves and associated branches, and dorsal genital nerves. In some examples, IMD 16 delivers the electrical stimulation therapy to a sacral nerve of patient 14 to inhibit bladder contractions. Although not specifically illustrated in FIG. 1A, in some examples, IMD 16 may be implanted to deliver the electrical stimulation therapy to a tibial nerve of patient 14.

IMD 16 is configured to provide electrical stimulation therapy to patient 14 by generating and delivering electrical stimulation signals to a target therapy site within patient 14 by lead 28 and, more particularly, via electrodes 29A-29D (collectively referred to as "electrodes 29"), which can be disposed proximate to a distal end of lead 28 in some examples. For example, IMD 16 may deliver electrical stimulation therapy to patient 14 according to therapy parameters, such as therapy parameters that result in subsensory electrical stimulation.

As one example, patient 14 may undergo a therapy induction phase and a therapy maintenance phase. The therapy induction phase may be to identify the therapy parameters that provide electrical stimulation at the sensory threshold. As described above, sensory threshold refers to the minimum electrical stimulation level at which a particular physiological response occurs (e.g., where patient 14 perceives to the electrical stimulation by feeling the stimulation, by motor movement, or by generating a detectable EMG signal or an eCAP of sufficient amplitude, as a few non-limiting examples). In some examples, IMD 16 may be configured to continuously deliver sensory electrical stimulation at the sensory threshold to patient 14. The delivery of the sensory electrical stimulation at the sensory threshold may result in a therapeutic effect for incontinence therapy. In some examples, the therapy induction phase includes a plurality of days or weeks after implantation of IMD 16 within patient 14. For example, the therapy induction phase includes at least four weeks after implantation of IMD 16 within patient 14.

During the therapy maintenance phase, IMD 16 may be configured to deliver subsensory electrical stimulation. As described above, subsensory electrical stimulation refers to electrical stimulation where the particular physiological response that occurred at the sensory threshold does not occur. For example, with subsensory electrical stimulation, patient 14 may not perceive the electrical stimulation (e.g., one or more of may not feel the stimulation, may not have a motor movement, and/or may not generate an electrical signal). During the therapy maintenance phase, patient 14 may receive subsensory electrical stimulation but the subsensory electrical stimulation may be efficacious in providing therapy. As described in more detail, in some examples, IMD 16 may cycle delivery of the subsensory electrical stimulation to patient 14.

Patient 14 generating a physiological response (e.g., for electrical stimulation at or greater than sensory threshold) or not generating a physiological response (e.g., for subsensory electrical stimulation) should not be confused with efficacy of therapy. For instance, patient 14 may experience effective therapy for incontinence when the electrical stimulation is at or greater than the sensory threshold. In accordance with one or more examples described in this disclosure, patient 14 may also experience effective therapy for incontinence when the electrical stimulation is subsensory electrical stimulation. For example, IMD 16 may be configured to deliver the subsensory electrical stimulation (e.g., to at least one of a sacral nerve or tibial nerve) to provide immediate therapeutic effect caused by the ongoing delivery of the subsensory electrical stimulation to address incontinence. For instance, the subsensory electrical stimulation may not cause a delayed effect, where patient 14 experiences therapy for incontinence after the subsensory electrical stimulation ceases.

In some examples, IMD 16 may be configured to deliver subsensory electrical stimulation based on cycle settings, sensor data, and/or patient input. As one example, IMD 16 may detect a bladder contraction based on sensor data and then deliver electrical stimulation (e.g., subsensory electrical stimulation) based on the detected bladder contraction. As another example, patient 14 may use external programmer 24 to provide input to IMD 16 (e.g., indicating an increased probability of unintentional voiding), and IMD 16 may deliver the electrical stimulation (e.g., subsensory electrical stimulation) to patient 14 to inhibit bladder contraction based on the patient input.

In some examples, in addition to electrical stimulation therapy, IMD 16 may also be configured to provide reminder electrical stimulation to patient 14 by generating and delivering electrical stimulation signals to a target therapy site by lead 28 and, more particularly, via one or more selected electrodes 29. The reminder electrical stimulation may be referred to as electrical reminder therapy. For example, IMD 16 may deliver the reminder electrical stimulation to patient 14 at predetermined intervals and in the form of reminder pulses. In some examples, reminder electrical stimulation may include the delivery of electrical signals to a target therapy site for the purpose of reminding patient 14 to voluntarily void, or for the purpose of reminding patient 14 of the existence of the electrical stimulation therapy (e.g., reminding patient 14 that IMD 16 is implanted in patient 14 and delivers electrical stimulation therapy to patient 14). The use of a reminder electrical stimulation is provided as merely one example and should not be considered limiting. Example techniques for cycling therapy and providing reminder electrical stimulation is described in U.S. Patent Publication No. 2017/0239470, the contents of which are incorporated by reference in their entirety.

For cycling of the subsensory electrical stimulation, IMD 16 may be configured to cycle delivery of the subsensory electrical stimulation to patient 14, between an on-cycle and an off-cycle, according to a cycle ratio of between 2% to more than 75%, such as between about 2% and 50% or 33% and 50%. An on-cycle refers to an amount of time during which IMD 16 is actively delivering the subsensory electrical stimulation, and an off-cycle refers to an amount of time during which IMD 16 is not actively delivering the subsensory electrical stimulation. The cycle ratio may be computed as the on-cycle divided by the result of the summation of the on-cycle plus the off-cycle.

During the on-cycle (e.g., when IMD 16 is actively delivering the subsensory electrical stimulation), IMD 16 may deliver pulses or series of pulses of electrical stimulation. In between the pulses, there may be instances where the amplitude of the electrical stimulation is zero or near zero. Although there may be times when the amplitude of the electrical stimulation is zero or near zero during the on-cycle, IMD 16 may still be considered as actively delivering the subsensory electrical stimulation. During the off-cycle, IMD 16 may cease delivery of subsensory electrical stimulation or deliver such a low level of electrical stimulation that there is no physiological change that causes patient 14 to void or not void.

As an example, IMD 16 may deliver subsensory electrical stimulation at a frequency of 10 Hz, where the pulses have a pulse width of 20 milliseconds, during the on-cycle. In this example, IMD 16 may deliver an electrical stimulation pulse for 20 milliseconds, not deliver for 80 milliseconds, then deliver an electrical stimulation pulse for 20 milliseconds, and so on for the on-cycle. Although there are instances where the amplitude of the electrical simulation is zero or near zero (e.g., for 80 milliseconds every 100 milliseconds) during the on-cycle, IMD 16 may still be considered as actively delivering subsensory electrical stimulation. Also, during this on-cycle, the amplitude of the electrical stimulation may be high enough to provide therapeutic effect but low enough that patient 14 does not perceive the electrical stimulation.

IMD 16 may be surgically implanted in patient 14 at any suitable location within patient 14, such as near the pelvis or possibly in the ankle for tibial stimulation. In some examples, the implantation site may be a subcutaneous location in the side of the lower abdomen or the side of the lower back or upper buttocks. IMD 16 has biocompatible housing 40, which may be formed from titanium, stainless steel, a liquid crystal polymer, or the like. The proximal ends of leads 18, 20, and 28 are electrically and mechanically coupled to IMD 16 either directly or indirectly (e.g., via one or more respective lead extensions). Electrical conductors disposed within the lead bodies of leads 18, 20, and 28 electrically connect sense electrodes (not shown) and stimulation electrodes, such as electrodes 29, to a therapy delivery circuitry (e.g., a stimulation generator) within IMD 16. In the example of FIG. 1, leads 18 and 20 carry electrodes 19A, 19B (collectively referred to as "electrodes 19") and electrodes 21A, 21B (collectively referred to as "electrodes 21"), respectively. As described in a further detail below, electrodes 19 and 21 may be positioned for sensing an impedance of bladder 12, which may decrease as the volume of urine within bladder 12 increases.

One or more medical leads (e.g., leads 18, 20, and 28), may be connected to IMD 16, and may be surgically or percutaneously tunneled to position one or more electrodes carried by a distal end of the respective lead at a desired pelvic nerve or muscle site (e.g., one of the previously listed target therapy sites such as a sacral or pudendal nerve). Stimulation at other nerves such as tibial nerve may be possible by surgically positioning, through the ankle of patient 14, one or more electrodes near the tibial nerve. The one or more electrodes may be on a lead or may be leadless (e.g., where the electrodes are formed on IMD 16).

In some examples, therapy system 10A includes one or more additional leads that each include one or more electrodes for sensing one or more physiological parameters, or one or more other types of sensors for sensing one or more physiological parameters. For example, in FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10A, IMD 16 may be coupled to more than one lead, each of which may include one or more electrodes for the delivery of electrical stimulation to different stimulation sites within patient 14 (e.g., to target different nerves).

Electrodes 29 may provide bipolar, multipolar, or unipolar stimulation. Bipolar stimulation refers to examples where one of electrodes 29 on lead 28 is the anode and another one of electrodes 29 is a cathode. Multipolar stimulation refers to examples where more than two electrodes 29 are used for stimulation. Unipolar stimulation refers to examples where one of electrodes 29 is the cathode and housing 40 includes an electrode that is the anode.

In the example shown in FIG. 1, leads 18, 20, and 28 are cylindrical. Electrodes 19, 21, and 29 of leads 18, 20, and 28, respectively, may be ring electrodes, segmented electrodes, or partial ring electrodes. Segmented and partial ring electrodes each extend along an arc less than 360 degrees (e.g., 90-120 degrees) around the outer perimeter of the respective lead 18, 20, 28. In some examples, one or more of leads 18, 20, and 28 may be, at least in part, paddle-shaped (i.e., a "paddle" lead), and may include pad electrodes positioned on a distal paddle surface.

In some examples, one or more of electrodes 19, 21, and 29 may be cuff electrodes that are configured to extend at least partially around a nerve (e.g., extend axially around an outer surface of a nerve). Depending on the target therapy delivery site and the particular patient, delivery of electrical stimulation by IMD 16 via one or more cuff electrodes, and/or segmented electrodes, may help achieve a more uniform electrical field or activation field distribution relative to the target nerve, thereby minimizing discomfort to patient 14 that may result from the delivery of electrical stimulation therapy.

The illustrated numbers and configurations of leads 18, 20, and 28 and the electrodes carried thereon are merely one example. Other configurations that may include various numbers and positions of the leads and electrodes also are possible. For example, IMD 16 may be coupled to additional leads or lead segments having one or more electrodes positioned at different locations in the pelvic region of patient 14. The additional leads may be used for delivering stimulation therapies to respective stimulation sites within patient 14, or may be used for monitoring one or more physiological parameters of patient 14. In examples in which the target therapy sites for the stimulation therapies are different, IMD 16 may be coupled to two or more leads, as may be required for bilateral or multi-lateral stimulation. In another example, IMD 16 may be coupled to fewer leads (e.g., to lead 28 only).

In some examples, IMD 16 may deliver electrical stimulation therapy based on patient input. In some examples, patient 14 may provide patient input using external programmer 24, or by tapping on the surface of the skin located over IMD 16, when IMD 16 includes a motion sensor that is responsive to tapping. In such examples, patient 14 may provide input to IMD 16 that indicates an urge felt by the patient, a leakage incident experienced by the patient, an imminent voiding event predicted by the patient, or a voluntary voiding event to be undertaken by the patient. In this way, therapy system 10A may provide patient 14 with direct control of the stimulation therapy delivered by IMD 16, which may improve the physiological and/or psychological treatment outcomes of patient 14.

In the illustrated example of FIG. 1, IMD 16 determines an impedance through bladder 12, which may vary as a function of the volume of urine present in bladder 12 and the contraction state of bladder 12. In such examples, the impedance of bladder 12 may be sensed via electrodes 19 and 21, which may be positioned on leads 18 and 20, respectively. In the example shown in FIG. 1A, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal; e.g., a current, through bladder 12 via leads 18 and 20, and determine bladder impedance based on a measured value of the transmitted electrical signal.

In the four-wire arrangement shown in FIG. 1, electrodes 19A and 21A and electrodes 19B and 21B may be located substantially opposite each other relative to the center of bladder 12. For example, electrodes 19A and 21A may be placed on opposing sides of bladder 12, either anterior and posterior or left and right. In FIG. 1, electrodes 19A, 19B and 21A, 21B are shown placed proximate to an exterior surface of the wall of bladder 12. In other examples, electrodes 19A, 19B and 21A, 21B may be sutured or otherwise affixed to the bladder wall, or may be implanted within the bladder wall. To measure the impedance of bladder 12, IMD 16 may source an electrical signal, such as an electrical current, to electrode 19A via lead 18, while electrode 21A via lead 20 sinks the electrical signal. IMD 16 then may determine a voltage measurement between electrodes 19B and 21B via leads 18 and 20, respectively. IMD 16 then may determine the impedance of bladder 12 using a known value of the electrical signal sourced and the determined voltage.

In the example of FIG. 1, IMD 16 includes a sensor comprising sensing circuitry 22 for detecting changes in the contraction of bladder 12. Sensing circuitry 22 may include, for example, one or more pressure sensors configured to detect changes in bladder pressure, one or more electrodes for sensing pudendal or sacral afferent nerve signals, one or more electrodes for sensing detrusor muscle or urinary sphincter (electromyograph) EMG signals, or any combination thereof. In some examples, sensing circuitry 22 may include one or more remote pressure sensors that wirelessly transmits signals to IMD 16, or may include one or more pressure sensors positioned on one or more of leads 18, 20, and 28. In such examples, a pressure sensor may include a detrusor pressure sensor or a sphincter pressure sensor. Such sensors may be configured to sense a contraction of a detrusor muscle or urethral sphincter of bladder 12 as an indication of a bladder fill level, patient sensation of an urge to void or other sensation related to voiding, or other physiological indication of bladder function. In other examples, sensing circuitry 22 may include one or more sense electrodes configured to sense afferent nerve signals. In such examples, the sense electrodes may be positioned on one or more of leads 18, 20, and 28. In examples in which sensing circuitry 22 includes one or more electrodes configured to sense a detrusor muscle or urinary sphincter EMG signal, such electrodes may be carried on one or more of leads 18, 20, and 28. In any of the examples described above, IMD 16 may control the delivery of electrical stimulation based on input received from bladder sensing circuitry 22. For example, IMD 16 may initiate the delivery of electrical stimulation to inhibit the contraction of bladder 12 when sensing circuitry 22 indicates an increase in the probability of an involuntary voiding event of patient 14, such as when an increase in bladder pressure or a change in muscle activity is detected by sensing circuitry 22.

In other examples, sensing circuitry 22 may include a patient motion sensor that generates a signal indicative of patient activity level or posture state. In some examples, in addition to delivering subsensory electrical stimulation, IMD 16 controls the delivery of stimulation therapy to patient 14 based on a sensed patient activity level or a patient posture state. For example, a patient activity level that is greater than or equal to a threshold may indicate that there is an increase in urgency and/or an increase in the probability that an incontinence event will occur, and accordingly, IMD 16 may provide electrical stimulation based on the patient activity level. In one example, the IMD 16 may deliver electrical stimulation to inhibit bladder contractions in response to a patient activity level that is greater than a threshold value, since there may be an increase in urgency and/or an increase in the probability that an incontinence event may occur. The inhibition of bladder contractions due to the delivery of electrical stimulation may reduce the probability that an incontinence event may occur.

As an additional example, patient 14 may be more prone to an incontinence event when in an upright posture state compared to a horizontal (i.e., lying down) posture state. Accordingly, in some examples, IMD 16 may be configured to deliver electrical stimulation to patient 14 based on the patient posture state sensed by sensing circuitry 22. For example, IMD 16 may deliver electrical stimulation to inhibit bladder contractions when sensing circuitry 22 senses that patient 14 is in a posture that is more prone to an incontinence event in order reduce the probability of an incontinence event.

As another example, sensing circuitry 22 may generate a signal indicative of patient motion. Processing circuitry of IMD 16 or programmer 24 then may determine, based on a pattern in the motion signal and/or other sensed parameters (e.g., bladder impedance), whether patient 14 voluntarily voided, involuntarily voided, or that an involuntary voiding event may be imminent.

Additionally, in other examples, sensing circuitry 22 may include a motion sensor that detects patient input, such as patient 14 tapping over the location in which IMD 16 is implanted, and causes processing circuitry of IMD 16 to control IMD 16 to deliver or suspend electrical stimulation therapy based on the patient input. In such examples, the processing circuitry may be configured to recognize various motion patterns, each of which may be associated with different inputs. For example, sensing circuitry 22 may be configured to detect a predetermined number or pattern of taps indicative of patient request, such as a request to suspend electrical stimulation therapy or a request to deliver electrical stimulation therapy. In other examples, such input may be received by programmer 24 and transmitted to processing circuitry of IMD 16.

System 10A includes an external programmer 24, as shown in FIG. 1. In some examples, programmer 24 may be a wearable communication device, handheld computing device, computer workstation, or networked computing device. As described in further detail below with respect to FIG. 4, programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user, such as patient 14, a caregiver, or a clinician, may interact with programmer 24 via the touch screen display. It should be noted that the user may also interact with programmer 24 and/or IMD 16 remotely via a networked computing device.

IMD 16 and programmer 24 may communicate via wireless communication using any techniques known in the art. Examples of communication techniques may include, for example, include radiofrequency (RF) telemetry, which may be an RF link established via an antenna according to Bluetooth, WiFi, or medical implant communication service (MICS), although other techniques are also contemplated. In some examples, programmer 24 may include a programming head that may be placed proximate to the patient's body near the IMD 16 implant site, in order to improve the quality or security of communication between IMD 16 and programmer 24.

In some examples, patient 14 may interact with programmer 24 to control IMD 16 to deliver the stimulation therapy, to manually abort the delivery of the stimulation therapy by IMD 16 while IMD 16 is delivering the therapy or is about to deliver the therapy, or to inhibit the delivery of the stimulation therapy by IMD 16, e.g., during voluntary voiding events. Patient 14 may, for example, use a keypad or touch screen of programmer 24 to cause IMD 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

In some examples, patient 14 may interact with programmer 24 to terminate the delivery of the stimulation therapy during voluntary voiding events, or to modify the type of stimulation therapy that is delivered (e.g., to control IMD 16 to deliver stimulation therapy to help patient 14 voluntarily void in examples in which patient 14 has a urinary retention disorder). That is, patient 14 may use programmer 24 to enter input that indicates the patient will be voiding voluntarily. When IMD 16 receives the input from programmer 24, IMD 16 may suspend delivery of the stimulation therapy for a predetermined period of time (e.g., two minutes), to allow the patient to voluntarily void, or switch to a different type of stimulation therapy to help patient 14 voluntarily void.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16 (e.g., select values) for the stimulation parameter values of one or more cycle settings with which IMD 16 generates and delivers electrical stimulation and/or the other operational parameters of IMD 16. For example, the user may use programmer 24 to retrieve information from IMD 16 regarding the contraction of bladder 12 and voiding events, including data contained in a voiding diary stored by IMD 16. As another example, the user may use programmer 24 to retrieve information from IMD 16 regarding the performance or integrity of IMD 16 or other components of system 10A, such as leads 18, 20, and 28, or a power source of IMD 16.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

As described above, IMD 16 may be configured to provide subsensory electrical stimulation. One example way in which to determine the therapy parameters for the subsensory electrical stimulation is to first determine the therapy parameters for electrical stimulation at the sensory threshold, and then adjust the therapy parameters so that IMD 16 delivers subsensory electrical stimulation. As described above, patient 14 may undergo a therapy induction phase and a therapy maintenance phase. In the therapy induction phase, patient 14 may be implanted with one or more leads, like one or more leads 18, 20, and 28, but may not yet be implanted with IMD 16. Rather, the implanted one or more leads may have a connection outside the body of patient 14 to which an external medical device couples. A clinician may cause the external medical device to deliver electrical stimulation at different levels to determine the sensory threshold (e.g., minimum electrical stimulation level at which effective treatment is still delivered to patient 14 and stimulation that patient 14 perceives).

For instance, the clinician may select a pulse width (e.g., 210 micro-seconds) and a frequency (e.g., 14 Hz) for the electrical stimulation, and select an amplitude at which patient 14 responds to the electrical stimulation. For example, patient 14 may perceive the stimulation such as by indicating that patient 14 is experiencing a "buzzing" feeling or a "thumping." In some cases, patient 14 may not feel the stimulation but there may be a physiological response. For instance, when stimulating one of a spinal nerve, sacral nerve, pudendal nerve, or the like, the physiological response may be a contraction of a toe of patient 14, a flexing of an anal sphincter of patient 14, or a detected EMG signal on an EMG. The clinician may reduce the amplitude until patient 14 no longer responds to the electrical stimulation.

The sensory threshold (also referred to as the physiological threshold stimulation intensity) may be defined as the stimulation intensity at which a physiological response of patient 14 is first observed when increasing the stimulation intensity (e.g., electrical stimulation level) from a relatively low intensity to a higher intensity (e.g., by manipulation of one or more parameters than contribute to intensity, such as amplitude, pulse rate, or pulse width). Stated another way, the sensory threshold may be defined as approximately the lowest stimulation intensity that causes an acute, physiologically significant, response of patient 14. In some examples, an acute response may be defined as a physiological response that occurs within about 30 seconds of patient 14 receiving the stimulation. In some examples, whether a response is physiologically significant may be defined by patient 14. As described above, the acute response may be a motor response, perceived response, or detected physiological response. In one example, the stimulation may cause a motor response in the form of movement of a toe of patient 14, and patient 14 may define the movement of the toe as physiologically significant when the movement of the toe is perceptible or when the movement of the toe is above some arbitrary amount defined by patient 14.

The stimulation intensity at which patient 14 no longer responds to the electrical stimulation (e.g., the acute response to the electrical stimulation does not occur) may be a subsensory electrical stimulation. During the therapy induction phase, patient 14 may not receive subsensory electrical stimulation. Accordingly, the clinician may slightly raise the intensity above the subsensory electrical stimulation until patient 14 perceives the electrical stimulation. Again, responding to electrical stimulation and effective treatment should not be confused. Patient 14 responding to electrical stimulation may mean that patient 14 is generating an acute physiological response to the stimulation therapy (e.g., feeling the stimulation, motor movement, detectable electrical signal generation), and patient 14 not responding to electrical stimulation may mean that patient 14 is not generating the particular acute physiological response. However, in both cases, it may be possible that patient 14 is experiencing effective incontinence therapy.

During the therapy induction phase, patient 14 may receive continuous electrical stimulation at the sensory threshold for a set amount of time (e.g., 7 to 14 days) to ensure that the incontinence therapy is effective. After ensuring that the incontinence therapy is effective, as part of the therapy induction phase, patient 14 may be implanted with IMD 16, and IMD 16 may be configured to deliver electrical stimulation at the sensory threshold, as determined by the clinician, using leads 18, 20, and/or 28. IMD 16 may deliver continuous electrical stimulation at the sensory threshold for a period of time (e.g., 4-6 weeks) to ensure that the therapy is effective. After the period of time, the therapy induction phase may be over, and patient 14 may undergo the therapy maintenance phase.

In this manner, IMD 16 may be configured to continuously deliver the sensory electrical stimulation at the sensory threshold to patient 14 based on a first set of therapy parameters during the therapy induction phase. The first set of therapy parameters may include amplitude, pulse width, and frequency. The continuous delivery of sensory electrical stimulation may mean that the stimulation is not cycling between on and off-cycles, but is rather always actively delivering therapy. The delivery of the sensory electrical stimulation at the sensory threshold results in a therapeutic effect for incontinence therapy. In some examples, the therapy induction phase includes at least four weeks after implantation of IMD 16 within patient 14. During the therapy induction phase, IMD 16 may continuously deliver therapy. However, there may be some examples in which IMD 16 cycles the delivery of electrical stimulation at the sensory threshold during the therapy induction phase, where cycling the delivery of electrical stimulation may include active delivery of electrical stimulation for an on-cycle and ceasing delivery of electrical stimulation for an off-cycle.

In accordance with one or more examples described in this disclosure, during the therapy maintenance phase, IMD 16 may be configured to deliver subsensory electrical stimulation. IMD 16 may be configured to deliver electrical stimulation where the stimulation intensity is approximately 90% to 10%, including approximately 50% or even lower of the stimulation intensity of the electrical stimulation during the therapy induction phase. IMD 16 may be configured to deliver electrical stimulation where the stimulation intensity is less than 50% to approximately 80% of the stimulation intensity of the electrical stimulation during the therapy induction phase. As one example, IMD 16 may be configured to deliver electrical stimulation where the stimulation amplitude is 50% of the amplitude of the electrical stimulation during the therapy induction phase. As another example, IMD 16 may be configured to deliver electrical stimulation where the pulse width is less than 50% of the pulse width of the electrical stimulation during the therapy induction phase.

In general, the amount by which the amplitude, pulse width, and/or frequency can be reduced in the therapy maintenance phase for subsensory electrical stimulation may be intertwined. As one example, if the amplitude is substantially reduced, then the pulse width and/or frequency may not be reduced by as much, and vice-versa to achieve approximately 90% to 10%, including 80% to 50%, and including approximately 50% and possibly lower, stimulation intensity.

There may be various ways in which IMD 16 may determine by how much to reduce the amplitude, pulse width, and/or frequency of the electrical stimulation at the sensory threshold to achieve the subsensory electrical stimulation. As one example, the electrical stimulation at the sensory threshold may be represented as a stimulation intensity. For instance, an integral of the electrical stimulation waveform over a time-period defined by the frequency may be indicative of the stimulation intensity for the therapy induction phase.

For the therapy maintenance phase, IMD 16 may be configured to deliver subsensory electrical stimulation having a stimulation intensity that is less than the stimulation intensity for the therapy induction phase. In some examples, the stimulation intensity for the therapy maintenance phase may be substantially less than the stimulation intensity for the therapy induction phase (e.g., where substantially less means less than approximately 90% of the stimulation intensity for the therapy induction phase). For instance, clinical data may indicate that if stimulation intensity for the therapy induction phase is reduced by approximately 20% to 50%, patient 14 may still experience effective therapy.

In some examples, the clinician may determine the sensory threshold with assistance from patient 14. After determining the sensory threshold, the clinician may determine therapy parameters that result in subsensory electrical stimulation and ensure that the subsensory electrical stimulation is not perceived by patient 14.

In some examples, it may be possible for IMD 16 to auto-determine a recommendation of therapy parameters. For instance, the IMD 16 may store information of a strength-duration curve (e.g., in a look-up table) that indicates what the pulse width, amplitude, and frequency should be to achieve different power levels. IMD 16 may select an amplitude (e.g., within a preconfigured range) or the clinician may input an amplitude value, and IMD 16 may determine what the pulse width and frequency should be to achieve the stimulation intensity for the therapy maintenance phase. As an example, assume that the stimulation intensity for the sensory threshold is X watts (W) for the therapy induction phase. In this example, IMD 16 may be configured to deliver electrical stimulation at a subsensory level such that the stimulation intensity is between 0.8*X to 0.2*X watts (e.g., 0.5*X watts) for the therapy maintenance phase. In some examples, stimulation intensity less than 0.5*X, including 0.2*X, may be possible. IMD 16 may select an amplitude or the clinician may input an amplitude, and IMD 16 may determine the pulse width and frequency using the strength-duration curve such that the resulting stimulation power is approximately (e.g., within 10%) the desired stimulation intensity for subsensory electrical stimulation. Example techniques for using the strength-duration curve are described in more detail with respect to FIG. 8.

In the above example, IMD 16 may select an amplitude or the clinician may input an amplitude. In some examples, IMD 16 may select a pulse width and/or frequency or the clinician may input a pulse width and/or frequency and IMD 16 may determine the amplitude. Also, in some examples, rather than IMD 16 determining the amplitude, pulse width, and frequency for the subsensory electrical stimulation, the clinician may input the amplitude, pulse width, and/or frequency for the subsensory electrical stimulation.

In the therapy maintenance phase, IMD 16 may deliver subsensory electrical stimulation to provide patient 14 with effective therapy. In some examples, during the therapy maintenance phase, IMD 16 may be configured to cycle through therapy, rather than deliver continuous therapy. For example, IMD 16 may be configured to deliver subsensory electrical stimulation for X minutes (e.g., an on-cycle), and then not deliver therapy for Y minutes (e.g., an off-cycle), and then again deliver therapy for X minutes (e.g., an on-cycle), and so on. IMD 16 may repeat these operations during a certain time period of the day. For instance, IMD 16 may be configured to cycle on for 10 minutes and off for 10 minutes and may repeat these operations for 16 hours within a 24-hour time period. For the other 8 hours, IMD 16 may not deliver electrical stimulation unless instructed or in response to a sensed event. In some examples, IMD 16 may further be configured to deliver for only 30 minutes and not deliver therapy for the remaining 23 hours and 30 minutes.

In some examples, the on-cycle is approximately 8 hours and the off-cycle is approximately 16 hours. In some examples, the on-cycle is approximately 30 minutes and the off-cycle is approximately 30 minutes. In some examples, the on-cycle is approximately 1.5 hours and the off-cycle is approximately 1.5 hours.

Cycling delivery of the subsensory electrical stimulation may be based on a cycle ratio. The cycle ratio may be the on-cycle divided by the sum of the on-cycle and off-cycle. The cycle ratio may be in a range of 2% to more than 50%, including 75%. In some examples, the cycle ratio may be in a range of 33% to 50%. For example, if the on-cycle is 30 minutes and the off-cycle is 23 hours and 30 minutes (i.e., 1410 minutes), then the cycle ratio is equal to (30 minutes)/(30 minutes+1410 minutes), which is 2.08%. As another example, if the on-cycle is 8 hours and the off-cycle is 16 hours, then the cycle ratio is equal to (8 hours)/(8 hours+16 hours), which is 33%. As another example, if the on-cycle is 1.5 hours and the off-cycle is 1.5 hours, then the cycle ratio is equal to (1.5 hours)/(1.5 hours+1.5 hours), which is 50%.

Accordingly, IMD 16 may be configured to cycle delivery of the subsensory electrical stimulation to patient 14, between an on-cycle and an off-cycle, according to a cycle ratio of between about 2% and 75%, including between 2% and 50% and between 33% and 50%, based on a second set of therapy parameters during the therapy maintenance phase. The second set of therapy parameters may include amplitude, pulse width, and frequency for electrical stimulation that patient 14 does not perceive when delivered. For example, the subsensory electrical stimulation has a stimulation intensity in range of less than 50% to approximately 80% of the stimulation intensity at the sensory threshold (e.g., 20% to 80%, 30% to 80%, 40% to 80%, 50% to 80%, 60% to 80%, or 70% to 80%). The therapy maintenance phase immediately follows the therapy induction phase, and as described above, delivery of the subsensory electrical stimulation results in the therapeutic effect for the incontinence therapy, and patient 14 does not perceive delivery of the subsensory electrical stimulation.

As an example, during the therapy induction phase, electrical stimulation having amplitude of 1 mA, pulse width of 210 micro-seconds, and frequency of 14 Hz may provide electrical stimulation at the sensory threshold. During the therapy maintenance phase, for the subsensory electrical stimulation, IMD 16 may be configured to deliver electrical stimulation having amplitude of 0.8 mA, pulse width of 100 micro-seconds, and frequency of 14 Hz. The previous is merely one non-limiting example simply to assist with understanding and should not be considered limiting. For example, during therapy maintenance phase, for the subsensory electrical stimulation, IMD 16 may be configured to deliver electrical stimulation having amplitude of 0.8 mA, pulse width of 210 micro-seconds, and frequency of 14 Hz. Examples of the pulse width may be in range of 60 micro-seconds to 210 micro-seconds, and examples of the frequency may be in range of 5 Hz to 25 Hz.

During the therapy maintenance phase, it may be possible for patient 14 to revert back to electrical stimulation in which there is a sensory response. For instance, in the event that patient 14 experiences less than efficacious therapy or intermittent therapy, patient 14 may interact with programmer 24 to cause IMD 16 to deliver electrical stimulation having stimulation parameters that provide stimulation intensity that is equal to or greater than the stimulation intensity delivered during the therapy induction phase.

The above example of the therapy induction phase and the therapy maintenance phase is provided merely to assist with understanding and should not be considered as limiting. For instance, in some examples, the therapy induction phase may not include a time period where therapy is delivered with an external medical device. Rather, the surgeon may implant IMD 16, and the clinician, based on feedback from patient 14, may determine the sensory threshold. Also, rather than operating IMD 16 for a certain time period during the therapy induction phase at the sensory threshold, the clinician may set the therapy parameters for the subsensory electrical stimulation immediately or shortly after determining the sensory threshold.

Also, the amplitude of 1 mA, pulse width of 100 or 210 micro-seconds, and frequency of 14 Hz is provided as examples and should not be considered limiting. In some examples, the frequency may be in the range of 5 Hz to 130 Hz. As one example, the frequency may be in range of 5 Hz to 25 Hz. As one example, the frequency may be in range of 5 Hz to 14 Hz. As one example, the frequency may be in range of 14 Hz to 25 Hz. The frequency may be one of 5 Hz, 14 Hz, or 25 Hz.

In some examples, higher frequencies may also be used. For instance, the frequency may be in range of 500 Hz to 5 kHz. As one example, the frequency may be one of 500 Hz, 1 kHz, or 5 kHz. In one example, the frequency may be in range of 500 Hz to 1 kHz or in range of 1 kHz to 5 kHz.

The pulse width of 100 micro-seconds or 210 micro-seconds are examples. In some examples, having a lower pulse width may be beneficial as there may be a larger range of amplitude to select from as compared to examples where there is a higher pulse width. In other words, having a lower pulse width (e.g., 100 micro-seconds) allows for a first range of amplitudes that can be selected to achieve subsensory electrical stimulation, and having a higher pulse width (e.g., 400 micro-seconds) allows for a second range of amplitudes that can be selected to achieve subsensory electrical stimulation. The first range may be greater than the second range. However, utilizing lower pulse widths is not necessary and the example above is provided merely as one non-limiting example.

In this manner, IMD 16 may be configured to determine a first electrical stimulation level (e.g., first electrical stimulation intensity) at a sensory threshold at which a particular physiological response to electrical stimulation for incontinence treatment occurs. The first electrical stimulation level includes a first set of therapy parameters (e.g., a first amplitude, a first pulse width, and a first frequency). IMD 16 may be configured to determine a second electrical stimulation level (e.g., second electrical stimulation intensity) below the sensory threshold (e.g., determine a subsensory electrical stimulation) at which the particular physiological response does not occur. The second electrical stimulation level includes a second set of therapy parameters (e.g., a second amplitude, a second pulse width, and a second frequency, where one or more of the second amplitude, second pulse width, and second frequency are different than first amplitude, first pulse width, and first frequency).

As described above, patient 14 may not perceive delivery of the subsensory electrical stimulation and perceives delivery of stimulation at the sensory threshold. As one example, when delivering electrical stimulation having stimulation intensity at the sensory threshold, patient 14 may feel the electrical stimulation. In this example, when delivering subsensory electrical stimulation, patient 14 may not feel the electrical stimulation. As another example, when delivering electrical stimulation having stimulation intensity at the sensory threshold, patient 14 may respond to the electrical stimulation with a motor response (e.g., generate a motor response). In this example, when delivering subsensory electrical stimulation, patient 14 may not respond to the electrical stimulation with a motor response. As another example, when delivering electrical stimulation having stimulation intensity at the sensory threshold, patient 14 may generate an electrical signal such as a nerve action potential (e.g., EMG signal or eCAP). In this example, when delivering subsensory electrical stimulation, patient 14 may not generate the electrical signal.

Accordingly, when delivering therapy at or above the sensory threshold, patient 14 may have an acute physiological response such as a motor response, patient feeling, or a detected physiological effect such as a bioelectrical signal (e.g., sensed nerve action potential, EMG, or eCAP). When delivering therapy below the sensory threshold (e.g., subsensory electrical stimulation), patient 14 may not have the acute physiological response.

It should be understood that the above describes different examples of sensory threshold and subsensory electrical stimulation. The different examples may be applied separately or together. For instance, in some examples, patient 14, the clinician, and/or IMD 16 may determine only one sensory threshold (e.g., one of intensity where patient 14 feels the stimulation, intensity where there is a motor response, or intensity where patient 14 generates an electrical signal). In such examples, IMD 16 may be configured to deliver subsensory electrical stimulation that is at an intensity level less than the intensity level of the sensory threshold. In some examples, patient 14, the clinician, and/or IMD 16 may determine multiple sensory thresholds (e.g., two or more of intensity where patient 14 feels the stimulation, intensity where there is a motor response, or intensity where patient 14 generates an electrical signal). In such examples, IMD 16 may be configured to deliver subsensory electrical stimulation that is at a level less than both or each of two or more of the intensity levels of the two or more sensory thresholds.

In one or more examples, to determine the second electrical stimulation level (e.g., subsensory electrical stimulation), IMD 16 may be configured to determine a second set of therapy parameters (e.g., second amplitude, a second pulse width, and a second frequency). Two or more of the first amplitude, first pulse width, and first frequency may be different than the second amplitude, second pulse width, and second frequency. For example, the first amplitude and first pulse width may be different than the second amplitude and second pulse width, respectively.

As described above, the clinician may identify the sensory threshold (e.g., by titrating stimulation intensity upwards or downwards). In some examples, IMD 16 may be configured to identify the sensory threshold, such as based on determining if there is any motor movement (e.g., based on accelerometers located on patient 14) or sense nerve action potential. The clinician or IMD 16 may then determine parameters for subsensory electrical stimulation (e.g., 80%, 50%, or 20% of the stimulation parameters at the sensory threshold).

In this way, IMD 16 may be configured to store a set of therapy parameters for subsensory electrical stimulation of a patient. Delivery of the subsensory electrical stimulation results in a therapeutic effect for incontinence therapy at a stimulation intensity that is less than or equal to 90% of a stimulation intensity at a sensory threshold (e.g., range of 90% to 10%, including 50% or lower, a range of 80% to 50%, etc.). Patient 14 does not perceive delivery of the subsensory electrical stimulation and perceives delivery of stimulation at the sensory threshold.

In the above examples, during the therapy induction phase, electrical stimulation is continuously delivered at the sensory threshold. In some examples, instead of or in addition to the continuous delivery of electrical stimulation, stochastic stimulation may be delivered to patient 14. Stochastic stimulation refers to a pattern of applying different stimulation intensities to patient 14. In some examples, rather than following a pattern, the application of different stimulation intensities may be random or pseudo-random.

In addition to stochastic stimulation, some form of closed loop stimulation may be used in the therapy induction phase. Additionally, closed loop stimulation may be used during maintenance phase as well, in addition to or instead of cycling or continuous stimulation. Closed loop stimulation relies on any of a variety of signals that form as feedback. As one example, in the subsensory electrical stimulation, patient 14 may not feel the stimulation but may still generate an electrical signal. In some examples, IMD 16 (e.g., via sensing circuitry 22 of FIG. 3) may sense the electrical signals (e.g., EMG signal or eCAP) and utilize the electrical signal to determine the therapy parameters. As another example, sensing circuitry 22 may determine the posture or the pressure or variety of other physiological signals to determine the therapy parameters for the subsensory electrical stimulation.

Figure 2:
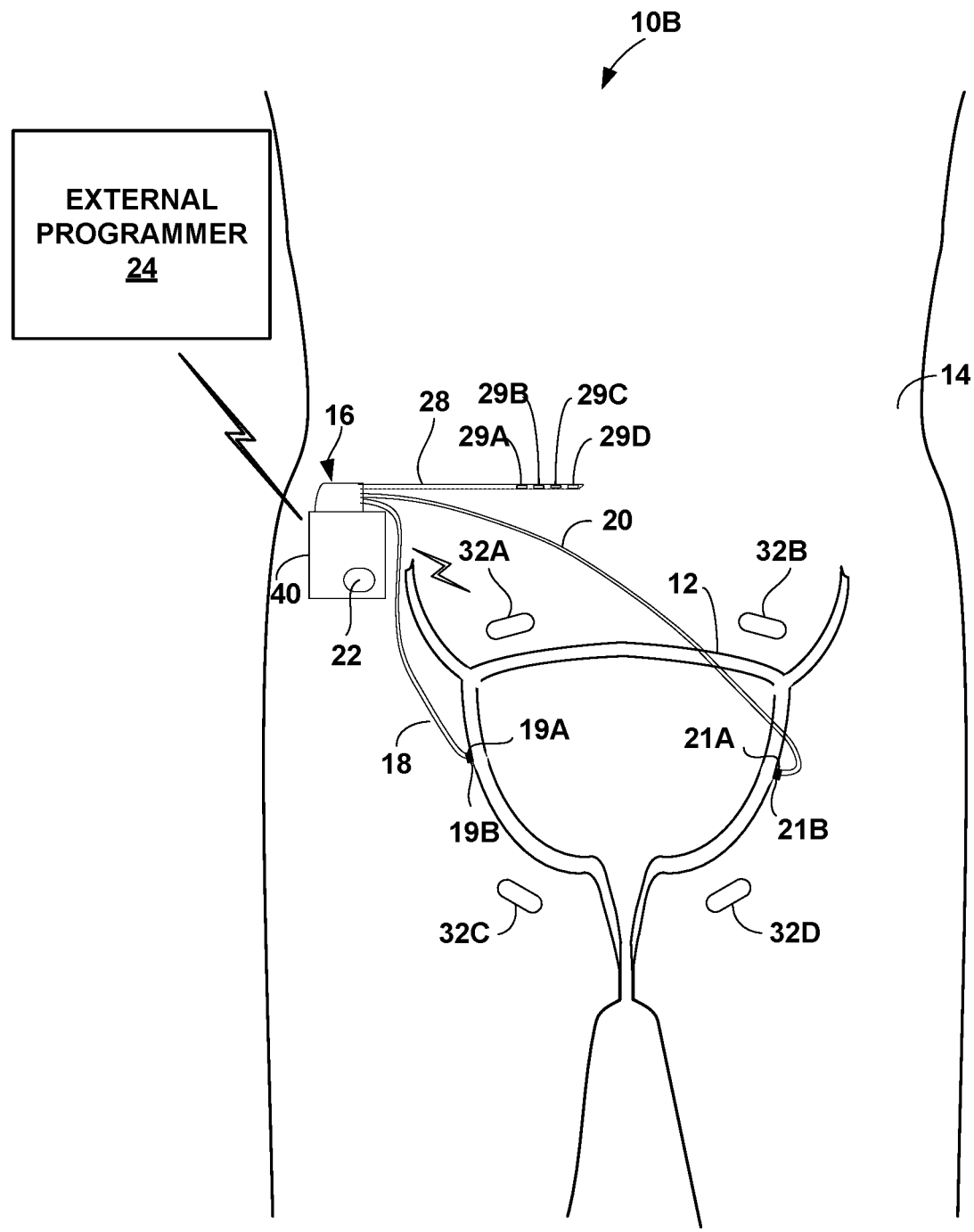
FIG. 2 illustrates, diagrammatically, a patient with another example implanted medical device including a therapy delivery circuitry.

FIG. 2 is conceptual diagram illustrating another example therapy system 10B that delivers stimulation therapy to manage, e.g., urinary incontinence or other condition of patient 14. Therapy system 10B includes a distributed array of electrical stimulators, referred to herein as microstimulators 32A-32D (collectively referred to herein as "microstimulators 32"), in addition to IMD 16, leads 18, 20, and 28, sensing circuitry 22, and programmer 24. In other examples, therapy system 10B includes a distributed array of microstimulators 32 instead of one or more of IMD 16, leads 18, 20, and 28, or sensing circuitry 22. Microstimulators 32 may be configured to generate and deliver electrical stimulation therapy (e.g., subsensory electrical stimulation) to patient 14 via one or more electrodes. Microstimulators 32 have a smaller size than IMD 16, and in some examples may be leadless.

IMD 16 may be configured to deliver electrical stimulation therapy (e.g., subsensory electrical stimulation) to patient 14 via microstimulators 32. For example, IMD 16 may communicate wirelessly with microstimulators 32 via wireless telemetry to control delivery of electrical stimulation to patient 14 via microstimulators 32. In the example of FIG. 2, microstimulators 32 may be implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible. For example, a microstimulator may be implanted in ankle of patient 14 for delivering stimulation to a tibial nerve, but stimulating the tibial nerve at locations other than the ankle may be possible.

Systems 10A and 10B shown in FIGS. 1 and 2, respectively, are examples of therapy systems that may each subsensory electrical stimulation and/or electrical stimulation therapy according to one or more cycle settings to manage urgency and/or urinary incontinence. Systems with other configurations of leads, electrodes, and sensors may also be used to implement the techniques described herein. Additionally, in other examples, a system may include more than one IMD 16.

Figure 3:
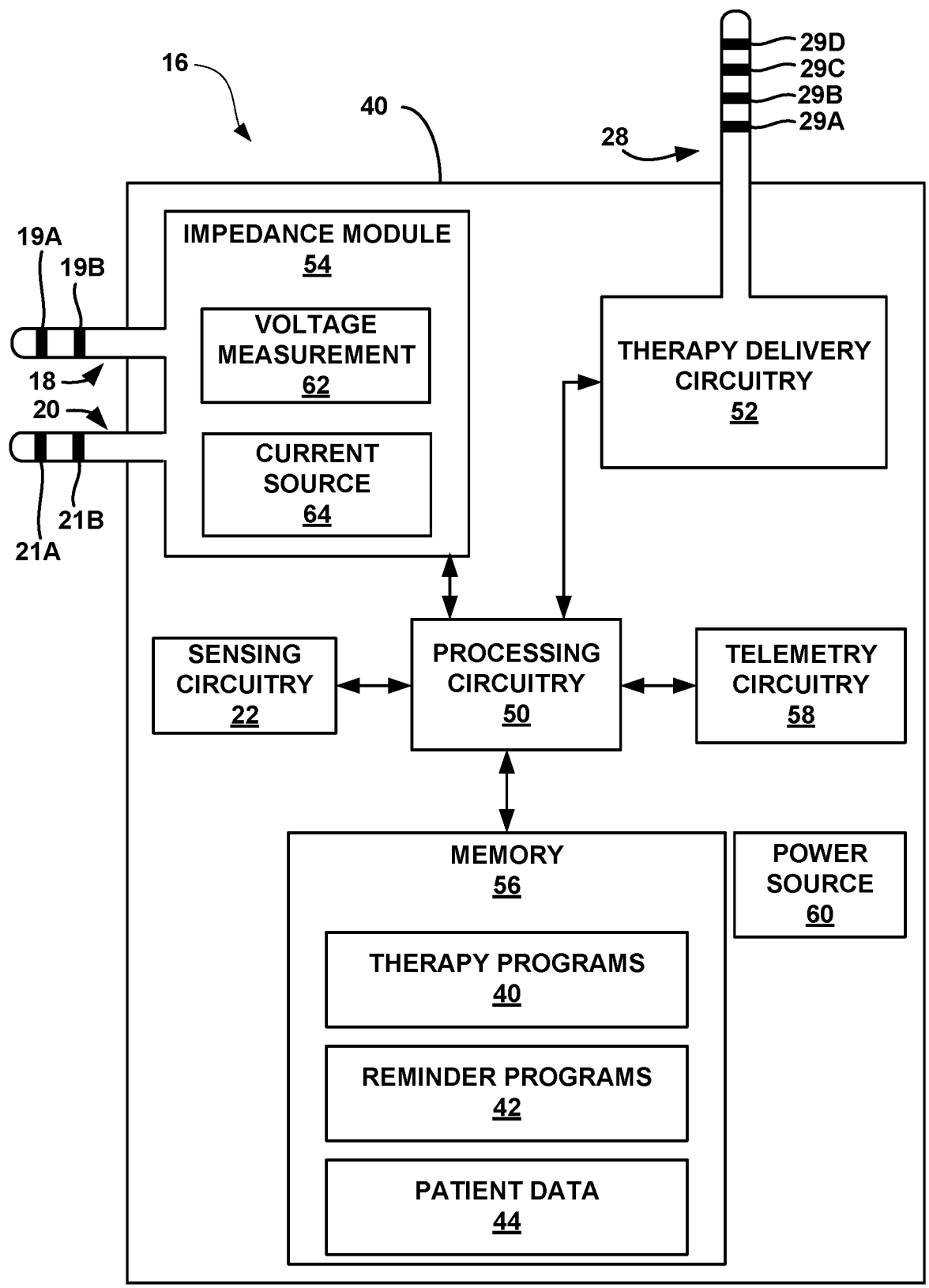
FIG. 3 is a functional block diagram illustrating an example configuration of the implantable medical device of FIGS. 1 and 2.

FIG. 3 is a functional block diagram of an example configuration of IMD 16. In the illustrated example, IMD 16 includes sensing circuitry 22, processing circuitry 50, therapy delivery circuitry 52, impedance module 54, memory 56, telemetry circuitry 58, and power source 60. In various examples, processing circuitry 50, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed to processing circuitry 50, as well as other processing circuitry described herein, herein may be embodied as hardware, firmware, software or any combination thereof.

Processing circuitry 50 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. Processing circuitry 50 may include arithmetic logic units (ALUs), elementary function units (EFUs), digital circuits, analog circuits, and/or programmable cores, formed from programmable circuits. In examples where the operations of processing circuitry 50 are performed using software executed by the programmable circuits, memory 56 may store the object code of the software that processing circuitry 50 receives and executes, or another memory within IMD 16 (not shown) may store such instructions.

In the example of FIG. 3, under the control of processing circuitry 50, therapy delivery circuitry 52 (which may also be referred to as a therapy delivery module) is configured to generate and deliver electrical stimulation via selected electrodes 29 of lead 28, alone or in combination with electrodes of another lead or of a housing 40 of IMD 16. For example, processing circuitry 50 may control therapy delivery circuitry 52 by accessing memory 56 to selectively access and load one or more therapy programs or reminder programs into therapy delivery circuitry 52. Therapy delivery circuitry 52 may include stimulation generation circuitry configured to generate and deliver electrical stimulation according to the one or more cycle settings or reminder therapy programs. Therapy delivery circuitry 52 may also be referred to as a stimulation generator.

In some examples, therapy delivery circuitry 52 generates therapy in the form of electrical pulses that are delivered using lead 28 and electrodes 29. In some examples, there may be two or more leads like lead 28 with respective electrodes 29 and therapy delivery circuitry 52 may form the electrical pulses that are delivered via the plurality of leads using respective electrodes of the leads. Relevant stimulation parameters for a therapy program may include a voltage amplitude, a current amplitude, a frequency (e.g., pulse rate), a pulse width, a duty cycle, or the combination of electrodes 29 with which therapy delivery circuitry 52 delivers the electrical stimulation signals to tissue of patient 14. In other examples, therapy delivery circuitry 52 may generate electrical stimulation in the form of continuous waveforms. In such examples, relevant stimulation parameters for a therapy program may include a voltage amplitude or a current amplitude, a frequency, a shape of the stimulation signal, a duty cycle of the stimulation signal, or the combination of electrodes 29 with which therapy delivery circuitry 52 delivers the electrical stimulation signals to tissue of patient 12.

In some examples, patient 14 may provide patient input to IMD 16 using programmer 24 or another device, or directly via IMD 16. For example, patient 14 may provide patient input to IMD 16 using sensing circuitry 22 when sensing circuitry 22 includes a motion sensor that is responsive to tapping (e.g., by patient 14) on skin superior to IMD 16. When sensing circuitry 22 includes a motion sensor that is responsive to tapping, upon detecting the pattern of tapping that indicates a particular patient input, processing circuitry 50 may determine that the patient input was received. The number, rate, or pattern of taps may be associated in memory 56 with the different programming capabilities. In this way, patient 14 may directly control the delivery of therapy by IMD 16 in the event that programmer 24 is not within reach of patient 14.

Regardless of whether patient input is received from programmer 24 or other device, the patient input may indicate an urge felt by patient 14, a leakage incident experienced by patient 14, an imminent voiding event predicted by patient 14, a voluntary voiding event undertaken by patient 14 or other information that may affect the timing or intensity level of electrical stimulation delivered by IMD 16. Throughout the disclosure, the term "intensity" is used to describe a level of electrical stimulation delivered to a patient. An intensity of stimulation may be a function of, for example, a current or voltage amplitude of the stimulation signal generated and delivered by IMD 16, the frequency of the stimulation signal, the shape of the stimulation signal, the duty cycle of the stimulation signal, the electrode combination used to deliver the stimulation signal, or any combination of the stimulation parameters. Thus, in some examples, intensity of stimulation may be modulated by modifying an amplitude of the electrical stimulation applied to the patient. Amplitude of electrical stimulation may refer to a magnitude of the voltage or current of a stimulation signal applied to the patient by IMD 16. For example, IMD 16 may increase/decrease a voltage and/or current delivered to the patient to increase/decrease the intensity of the electrical stimulation.

In the example of FIG. 3, therapy delivery circuitry 52 is electrically coupled to a single lead 28 but multiple leads could be used, and therapy delivery circuitry 52 delivers electrical stimulation to a tissue site of patient 14 via selected electrodes 29A-29D carried by lead 28 (e.g., a lead sized and configured for placement to stimulation sacral, such as within sacral foramen, pudendal, or other nerve). A proximal end of lead 28 extends from housing 40 of IMD 16, and a distal end of lead 28 extends to one or more target therapy sites, e.g., within a pelvic floor of patient 14. In some examples, target therapy sites may include tissue proximate a sacral nerve, a pudendal nerve, a hypogastric nerve, a tibial nerve, a urinary sphincter, or a detrusor muscle, although other target therapy sites may be used. In other examples, therapy delivery circuitry 52 may deliver electrical stimulation with electrodes on more than one lead and each of the leads may carry one or more electrodes. The leads may be configured as axial leads with ring electrodes and/or paddle leads with electrode pads arranged in a two-dimensional array. Additionally, or alternatively, the leads may include segmented and/or partial ring electrodes. The electrodes may operate in a bipolar or multi-polar configuration with other electrodes, or may operate in a unipolar configuration referenced to an electrode carried by outer housing 40 of IMD 16. In yet other examples, such as system 10B shown in FIG. 2 that includes microstimulators 32, processing circuitry 50 may act as a "master" module that controls microstimulators 32 to deliver stimulation at target therapy sites. In other examples, however, one of microstimulators 32 may act as a master module or microstimulators 32 may be self-controlled.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processing circuitry 50 may periodically control current source 64 to, for example, source an electrical current signal through electrode 19A and sink the electrical current signal through electrode 21A. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processing circuitry 50 determines an impedance value from the measured voltage values received from voltage measurement circuitry 52.

In examples in which sensing circuitry 22 includes a pressure sensor, processing circuitry 50 may determine a bladder pressure value based on signals received from the pressure sensor. Processing circuitry 50 may determine whether contractions of bladder 12 are indicative of an imminent incontinence event, for example, based on comparison of the sensed pressure to a pressure threshold that indicates an imminent event. For example, processing circuitry 50 may detect an imminent incontinence event when the sensed pressure is greater than the pressure threshold.

In some examples, sensing circuitry 22 may be configured to determine an amplitude or existence of an electrical signal generated by patient 14. For example, one or more of electrodes 29 of lead 28 may be sensing electrodes that sense electrical signals. Electrodes 29 may in some examples provide dual function of sensing and stimulation. Although not shown, sensing circuitry 22 may receive the sensed signals from one or more of electrodes 29 and determine whether patient 14 generated an electrical signal such as a nerve action potential (e.g., EMG signal or eCAP). In some examples, sensing circuitry 22 may receive signals from other components external to IMD 16. For example, patient 14 may wear an accelerometer that outputs a signal, via telemetry circuitry 58 and processing circuitry 50, to sensing circuitry that indicates whether there is motor movement from patient 14.

The threshold values stored in memory 56 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on patient input, e.g., via external programmer 24. As described above, patient 14 may indicate, via programmer 24, when an involuntary voiding event takes place. When the patient input is received, processing circuitry 50 may determine an impedance value during the event or immediately prior to the event based on signals received from impedance module 54. A new threshold value may be determined using this impedance value. For example, the threshold value stored may be a running average of impedance values measured during involuntary voiding events.

The threshold values stored in memory 56 may be a first set of therapy parameters for delivery of sensory electrical stimulation (e.g., during a therapy induction phase) and a second set of therapy parameters for delivery of subsensory electrical stimulation (e.g., during a therapy maintenance phase). For instance, an acute physiological response does not occur when the patient is stimulated with subsensory electrical stimulation. The first set of therapy parameters for sensory electrical stimulation includes a first amplitude, a first pulse width, and a first frequency. The second set of therapy parameters for subsensory electrical stimulation includes a second amplitude, a second pulse width, and a second frequency. In accordance with one or more examples described in this disclosure, two or more of the second amplitude, the second pulse width, and the second frequency are less than the first amplitude, the first pulse width, and the first frequency for electrical stimulation at a sensory threshold (e.g., sensory electrical stimulation). The acute physiological occurs in patient 14 in response to the electrical stimulation at the sensory threshold.

In this way, the threshold values stored in memory 56 may be a set of therapy parameters for sub sensory electrical stimulation of a patient. The delivery of the subsensory electrical stimulation results in a therapeutic effect for incontinence therapy at a stimulation intensity that is less than or equal to approximately 90% of a stimulation intensity at a sensory threshold (e.g., including stimulation intensity that is in range of less than 50% to approximately 80% of the stimulation intensity at the sensory threshold). Patient 14 does not perceive delivery of the subsensory electrical stimulation and perceives delivery of stimulation at the sensory threshold.

There may be various ways in which the first and second set of therapy parameters of subsensory electrical stimulation are generated and stored in memory 56. As one example, the clinician or patient 14 may use programmer 24 to program memory 56 with the first and second set of therapy parameters. As another example, processing circuitry 50 may receive information indicative of first set of therapy parameters (e.g., the first amplitude, the first pulse width, and the first frequency for electrical stimulation at the sensory threshold), and determine the second set of therapy parameters (e.g., second amplitude, the second pulse width, and the second frequency) based on the received information indicative of the first set of therapy parameters (e.g., first amplitude, the first pulse width, and the first frequency).

For example, based on the first amplitude, first pulse width, and first frequency, processing circuitry 50 may determine a stimulation intensity for the sensory threshold (e.g., integral of the amplitude over the pulse width multiplied by one divided frequency). Processing circuitry 50 may determine a stimulation intensity for the subsensory electrical stimulation (e.g., between 90% to 10% of the stimulation intensity of the sensory threshold) based on the stimulation intensity for the sensory threshold to determine the second set of parameters (e.g., second amplitude, second pulse width, and second frequency).

Processing circuitry 50 may then select the second amplitude, second pulse width, and second frequency such that the resulting simulation intensity is approximately, e.g., ±20%, of the determined stimulation intensity of the subsensory electrical stimulation. For example, memory 56 may store strength-duration curves that indicate what the appropriate amplitude should be for a given pulse width, and vice-versa for the subsensory electrical stimulation. Processing circuitry 50 may select an amplitude or pulse width and determine the other one of pulse width or amplitude based on the strength-duration curve.

In some examples, IMD 16 includes impedance sensing module 54 and not sensing circuitry 22, while in other examples IMD 16 includes sensing circuitry 22 but not impedance sensing module 54. Moreover, in some examples, sensing circuitry 22 and/or impedance sensing module 54 may be physically separate from IMD 16. Physically separate sensors may be useful in examples in which either sensing circuitry 22 and/or impedance sensing module 54 sense one or more physiological parameters at a location that is not accessible by IMD 16 or difficult to access by IMD 16. However, in other examples of IMD 16, IMD 16 may not include impedance module 54 or sensing circuitry 22 and may include other sensing circuitry or may not include any sensing circuitry configured to sense a patient parameter.

Processing circuitry 50 may control therapy delivery circuitry 52 to deliver electrical stimulation therapy based on patient input received via telemetry circuitry 58. Telemetry circuitry 58 includes any suitable hardware, firmware, software or any combination thereof for communicating with another device, such as programmer 24 of systems 10A and 10B. Under the control of processing circuitry 50, telemetry circuitry 58 may receive downlink telemetry, e.g., patient input, from and send uplink telemetry to programmer 24 with the aid of an antenna, which may be internal and/or external. Processing circuitry 50 may provide the data to be uplinked to programmer 24 and the control signals for the telemetry circuit within telemetry circuitry 58 and receive data from telemetry circuitry 58.

Processing circuitry 50 may control telemetry circuitry 58 to exchange information with medical device programmer 24. Processing circuitry 50 may transmit operational information and receive stimulation programs or stimulation parameter adjustments via telemetry circuitry 58. Also, in some examples, IMD 16 may communicate with other implanted devices, such as stimulators, control devices, or sensors, via telemetry circuitry 58.

Memory 56 stores instructions for execution by processing circuitry 50. Memory 56 may store one or more therapy programs for controlling delivery of electrical stimulation therapy by therapy delivery circuitry 52, one or more reminder programs, or both therapy programs and reminder programs. In some examples, memory 56 stores patient parameter information, such as information generated by impedance module 54 and/or sensing circuitry 22. For example, information related to measured impedance and determined posture may be recorded for long-term storage and retrieval by a user or used by processing circuitry 50 for adjustment of stimulation parameters, such as amplitude, pulse width, and pulse rate. Memory 56 may include separate memories for storing instructions, electrical signal information, stimulation programs, data pertaining to a voiding diary of patient 14, and other data.

In the example shown in FIG. 3, memory 56 stores therapy programs 40, reminder programs 42, and patient data 44. Therapy programs 40 store one or more therapy programs for use by processing circuitry 50 and therapy delivery circuitry 52 to control the delivery of electrical stimulation therapy to patient 14. In some examples, for each stored therapy program, the stored information may include parameters pertaining to the values of time X and time Y of a cycle setting of the therapy program, the electrode combination with which therapy delivery circuitry 52 delivers electrical stimulation to patient 14, and the electrical stimulation parameter values defining the electrical stimulation signal delivered to patient 14.

In some examples, it may be efficacious for IMD 16 to deliver electrical stimulation therapy according to a plurality of cycle settings over time. Cycle settings refer to turning off stimulation for a period of time (e.g., off-cycle) and then turning stimulation back on after a period of time (e.g., on-cycle). For example, IMD 16 may deliver electrical stimulation therapy according to a first cycle setting for a first period of time (a first cycle time period), and subsequently deliver electrical stimulation therapy according to one or more different cycle settings for additional respective periods of time. Thus, therapy programs 40 may store multiple cycle settings that can be selected by processing circuitry 50. Processing circuitry 50 may select the cycle setting by, for example, selecting a therapy program, which may include a cycle setting as part of its parameters, or by selecting a stored cycle setting, which can be stored in memory 56. In some examples, memory 56 may store a list of cycle settings in a predetermined order, and processing circuitry 50 may select cycle settings from the list in the predetermined order. Thus, at the end of a cycle time period or at another suitable time, processing circuitry 50 may select a next cycle setting to use to control delivery of electrical stimulation by therapy delivery circuitry 52 by selecting the next cycle setting in the preordered list.

As one example, therapy delivery circuitry 52 may be configured to cycle delivery of the subsensory electrical stimulation to patient 14, between an on-cycle and an off-cycle, according to a cycle ratio of between about 2% and 50%, based on the second set of therapy parameters during the therapy maintenance phase. The subsensory electrical stimulation may have a stimulation intensity in range of 2% to 80%, including less than 50% to approximately 80% of the stimulation intensity at the sensory threshold. Examples of the on-cycle and off-cycle include one of the following pairs: (1) the on-cycle is approximately 8 hours and the off-cycle is approximately 16 hours, (2) the on-cycle is approximately 30 minutes and the off-cycle is approximately 30 minutes, or (3) the on-cycle is approximately 1.5 hours and the off-cycle is approximately 1.5 hours. In some examples, the on-cycle may be 30 minutes and the off-cycle may be 23 hours and 30 minutes.

In other examples, memory 56 may store a list of cycle settings, and processing circuitry 50 may pseudo-randomly select cycle settings from the list, e.g., using a pseudo random counter, each number in the counter being associated with a stored cycle setting, or using any other suitable means. Thus, at the end of a cycle time period or at another suitable time, processing circuitry 50 may select a next cycle setting to use to control delivery of electrical stimulation by therapy delivery circuitry 52 by pseudo-randomly select cycle settings from a predetermined list of cycle settings.

Reminder programs 42 may include parameters pertaining to the timing, intensity, and duration of the electrical reminder therapy to be delivered to patient 14. Reminder therapy may be delivered to patient 14 as a reminder for patient 14 to voluntarily void, or as a reminder of the existence of therapy. Reminder programs 42 are optional.

In some examples, while IMD 16 is delivering subsensory electrical stimulation, patient 14 may desire to revert back to electrical stimulation at the sensory threshold, or possibly greater than the sensory threshold. For instance, if the subsensory electrical stimulation does not provide sufficient therapeutic effect or patient 14 desires to perceive the therapy, or possibly for some other reason, patient 14 may configure IMD 16 to deliver electrical stimulation at or greater than the sensory threshold. Memory 56 may also store the therapy parameters for delivering therapy at the sensory threshold. In such examples, in response to patient 14 requesting that therapy be delivered at the sensory threshold, processing circuitry 50 may cause therapy delivery circuitry 52 to deliver at the sensory threshold.

As illustrated, memory 56 stores patient data 44. Patient data 44 may include, for example, a voiding diary, physiological parameter values sensed by sensing circuitry 22, impedance module 54, or both, and any other suitable patient data 44.

In accordance with techniques described in this disclosure, the stimulation parameter values of a therapy program stored by memory 56 may define a therapy with an intensity below a perception threshold of the target tissue being stimulated. In other words, the simulation parameter values stored by memory 56 may be for subsensory electrical stimulation. For example, the electrical stimulation may have an intensity such that patient 14 does not feel the electrical stimulation delivered by IMD 16. As another example, the electrical stimulation may have an intensity such that the electrical stimulation delivered by IMD 16 does not result in a motor response from the patient. A motor response may be reported by the patient, observed by a clinician, or automatically detected by one or more sensors internal or external to the patient. An example of motor response can be, for example, an acute motor response, e.g., muscle twitch, inducted by the electrical stimulation. When stimulating one of a spinal nerve, sacral nerve, pudendal nerve, or the like, the physiological response may be a contraction of a toe of the patient, a flexing of an anal sphincter of the patient, or a detected EMG or eCAP signal.

In some examples, feeling of the stimulation by patient 14 may occur prior to an observed response of a muscle that is being driven by the nerve being stimulated. In other words, the feeling of the stimulation by patient 14 may occur at a lower intensity than the intensity at which patient 14 has a motor movement.

Accordingly, in one or more examples, patient 14 perceiving the delivery of stimulation at the sensory threshold may be patient 14 feeling the stimulation at the sensory threshold, and patient 14 not perceiving the delivery of subsensory electrical stimulation may be patient 14 not feeling the subsensory electrical stimulation. In one or more examples, patient 14 perceiving the delivery of stimulation at the sensory threshold may be patient 14 responding with a motor response to the stimulation at the sensory threshold, and patient 14 not perceiving the delivery of subsensory electrical stimulation may be patient 14 not responding to the subsensory electrical stimulation with the motor response. In one or more examples, patient 14 perceiving the delivery of stimulation at the sensory threshold may be patient 14 generating a detectable electrical signal (e.g., amplitude is high enough to be detected) in response to the stimulation at the sensory threshold, and patient 14 not perceiving the delivery of subsensory electrical stimulation may be patient 14 not generating the detectable electrical signal (e.g., amplitude is too low to be distinguished from other electrical signals) in response to the subsensory electrical stimulation.

Memory 56 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processing circuitry 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

As described above, by delivering electrical stimulation at a subsensory level, IMD 16 may consume less power from power source 60 as compared to IMD 16 delivering electrical stimulation at levels at or greater than the sensory threshold. Accordingly, by delivering electrical stimulation at subsensory levels, the longevity of power source 60 may be increased (e.g., in examples where power source 60 is not rechargeable) or the interval between recharges of power source 60 may be increased (e.g., in examples where power source 60 is rechargeable).

Although processing circuitry 50, therapy delivery circuitry 52, and telemetry circuitry 58 may be separate modules, in some examples, two or more of processing circuitry 50, therapy delivery circuitry 52, and telemetry circuitry 58 can be functionally integrated. In some examples, processing circuitry 50, therapy delivery circuitry 52, and telemetry circuitry 58 correspond to individual hardware units, such as ASICs, DSPs, FPGAs, or other hardware units.

Figure 4:
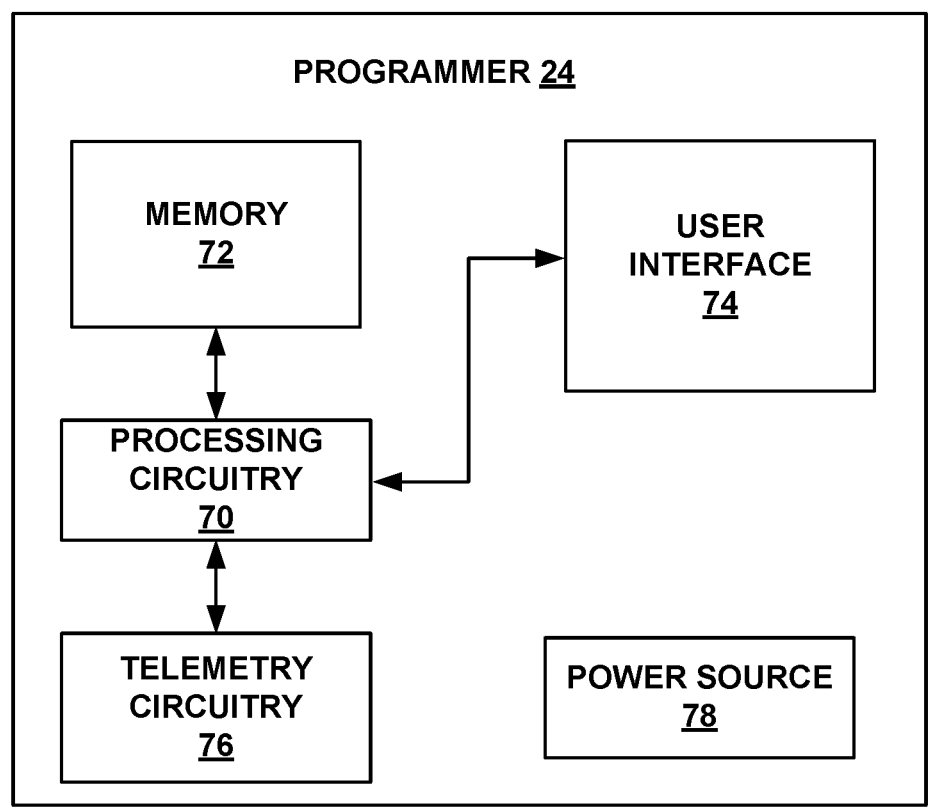
FIG. 4 is a functional block diagram illustrating an example configuration of the external programmer of FIGS. 1 and 2.

FIG. 4 is a functional block diagram illustrating example components of example external programmer 24. While programmer 24 may generally be described as a hand-held computing device, the programmer may be a notebook computer, a cell phone, or a workstation, for example. As illustrated in FIG. 4, external programmer 24 may include a processing circuitry 70, memory 72, user interface 74, telemetry circuitry 76, and power source 78. Memory 72 may store program instructions that, when executed by processing circuitry 70, cause processing circuitry 70 to provide the functionality ascribed to programmer 24 throughout this disclosure.

In some examples, memory 72 of programmer 24 may store a plurality of therapy programs defining one or more electrical stimulation parameter values and/or cycle settings for the delivery electrical stimulation therapy, similar to those stored in memory 56 of IMD 16. The therapy programs stored in memory 72 may be downloaded into memory 56 of IMD 16. Memory 72 may also include reminder programs defining one or more parameters for the delivery of electrical reminder stimulation. The reminder programs stored in memory 72 also may be downloaded into memory 56 of IMD 16.

Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processing circuitry 70 can take the form one or more microprocessors, DSPs, ASICs, FPGAs, programmable logic circuitry, or the like, and the functions attributed to processing circuitry 70 herein may be embodied as hardware, firmware, software or any combination thereof. Processing circuitry 70 may be similar to processing circuitry 50, but may in some examples, provide greater processing capabilities.

User interface 74 may include a button or keypad, lights, a speaker for voice commands, and a display, such as a liquid crystal (LCD). In some examples the display may be a touch screen. As discussed in this disclosure, processing circuitry 70 may present and receive information relating to stimulation therapy via user interface 74. For example, processing circuitry 70 may receive patient input via user interface 74. The patient input may be entered, for example, by pressing a button on a keypad or selecting an icon from a touch screen. Patient input may include, but is not limited to, input that indicates an urge felt by the patient, a leakage incident experienced by the patient, an imminent voiding event predicted by the patient, or a voluntary voiding event to be undertaken by the patient.

Telemetry circuitry 76 supports wireless communication between IMD 16 and external programmer 24 under the control of processing circuitry 70. Telemetry circuitry 76 may be substantially similar to telemetry circuitry 58 described above, providing wireless communication via an RF or proximal inductive medium. In some examples, telemetry circuitry 76 may include an antenna, which may take on a variety of forms, such as an internal or external antenna. An external antenna that is coupled to programmer 24 may correspond to a programming head that may be placed over IMD 16. Telemetry circuitry 76 may also be configured to communicate with another computing device via wireless communication techniques, or direct communication through a wired connection. Examples of local wireless communication techniques that may be employed to facilitate communication between programmer 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 24 without needing to establish a secure wireless connection.

Power source 78 delivers operating power to the components of programmer 24. In some examples, power source 78 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within programmer 24

Patient 14 may also interact with user interface 74 of programmer 24 to store data pertaining to voiding events in memory 72 of programmer 24 or memory 56 of IMD 16. In this manner, patient 14 may create a voiding diary that contains data indicating, for example, the number, frequency, and timing of involuntary voiding events. For example, patient 14 may enter, via a keypad or touch screen of user interface 74, an indication that an involuntary voiding event occurred at a particular time. Processing circuitry 70 of programmer 24 may correlate the timing of the voiding event with other data, such as the therapy program and/or specific cycle setting being used by IMD 16 at the time of the voiding events to deliver electrical stimulation therapy, patient posture data, patient activity data, and bladder impedance data sensed by impedance module 54 and sensing circuitry 22 at or shortly before the time of the voiding event.

Correlating involuntary voiding events with a particular therapy program or a particular cycle setting (multiple therapy programs may have the same cycle setting) may help control the timing with which processing circuitry 50 or 70 changes a currently implemented cycle setting. For example, processing circuitry 50 or 70 may compare the number of involuntary voiding events associated with a particular therapy program or a particular cycle setting with a predetermined threshold value (which may be stored in memory 56 or memory 72), and, in response to determining the number of involuntary voiding events is greater than or equal to the threshold value, processing circuitry 50 or 70 may control therapy delivery circuitry 52 to deliver therapy according to a different cycle setting. For example, as discussed below, the different cycle setting may be selected as the next cycle setting in a predetermined order of a plurality of cycle settings, or may be pseudo-randomly selected from a list of predetermined cycle settings.

In other examples, patient 14 may also interact with user interface 74 to cause memory 72 to store data pertaining to a voluntary voiding event or an increased urge event, which processing circuitry 70 may correlate with other data sensed by impedance module 54 or sensing circuitry 22 at the time of the voluntary voiding event or increased urge event. In other examples, processing circuitry 70 of programmer 24 may transmit the data regarding the patient input indicative of the occurrence of one or more voiding events to IMD 16, and processing circuitry 50 of IMD 16 may perform any of the functions described herein instead of processing circuitry 70.

In other examples, processing circuitry 50 may independently cause memory 56 of IMD 16 to store data pertaining to various urinary events, which may be sensed by IMD 16 (e.g., by sensing circuitry 22) or indicated by patient requests to deliver or suspend stimulation, which, as described above, may occur when patient 14 senses that an involuntary voiding episode may be imminent. In such examples, processing circuitry 50 may cause the data to be stored in the voiding diary as a record of the number, frequency, and timing of various urinary events, and, in some cases, as one or more physiological parameters sensed by sensing circuitry 22 or another sensing device. As with voiding data manually entered by patient 14 into programmer 24, processing circuitry 50 of IMD 16 may correlate the timing of a request for extra stimulation with other data, such as patient posture data, patient activity data, and bladder impedance data sensed by impedance module 54 and sensing circuitry 22 at or around the time of the event. Thus, a voiding diary of patient 14 may contain data entered by patient 14 and data independently stored by processing circuitry 50 and memory 56 of IMD 16, thereby providing a more robust representation of symptoms experienced by patient 14 than would be provided by patient-entered data or data independently stored by IMD 16 alone.

In some examples, programmer 24 may be a medical device configured to perform example techniques described in this disclosure. For example, a clinician and patient 14 may determine a first set of parameters that define a sensory threshold (e.g., a first amplitude, a first pulse width, and a first frequency). The clinician or patient 14 may enter the first set of parameters into programmer 24 via user interface 74 for storage in memory 72. As described, an acute physiological response occurs in patient 14 in response to the electrical stimulation at the sensory threshold being delivered to patient 14.

Processing circuitry 70 may be configured to determine a second set of therapy parameters (e.g., second amplitude, second pulse width, and second frequency) for subsensory electrical stimulation of the patient. The acute physiological response does not occur when patient 14 is stimulated with the subsensory electrical stimulation. As one example, processing circuitry 70 may be configured to determine the second set of therapy parameters such that the subsensory electrical stimulation is between 90% to 10% of a stimulation intensity at the sensory threshold (e.g., 80% to 20% or 80% to 50% or 50% of the stimulation intensity at the sensory threshold).

For instance, processing circuitry 70 based on the first amplitude, pulse width, and frequency may determine the stimulation intensity at the sensory threshold. Processing circuitry 70 may determine a stimulation intensity that is 90% to 10% or 80% to 50% of the stimulation intensity at the sensory threshold. Processing circuitry 70 may then select the second amplitude, second pulse width, and second frequency such that the resulting stimulation intensity is equal to the determined stimulation intensity for the subsensory electrical stimulation.

Processing circuitry 70 may output the second therapy parameters to telemetry circuitry 76 and cause telemetry circuitry 76 to output the second set of therapy parameters to IMD 16 for stimulating patient 14 with subsensory electrical stimulation. For example, memory 56 may store the set of therapy parameters determined by programmer 24 for subsensory electrical stimulation. Processing circuitry 50 may then cause therapy delivery circuitry 52 to deliver therapy for subsensory electrical stimulation.

Figure 5:
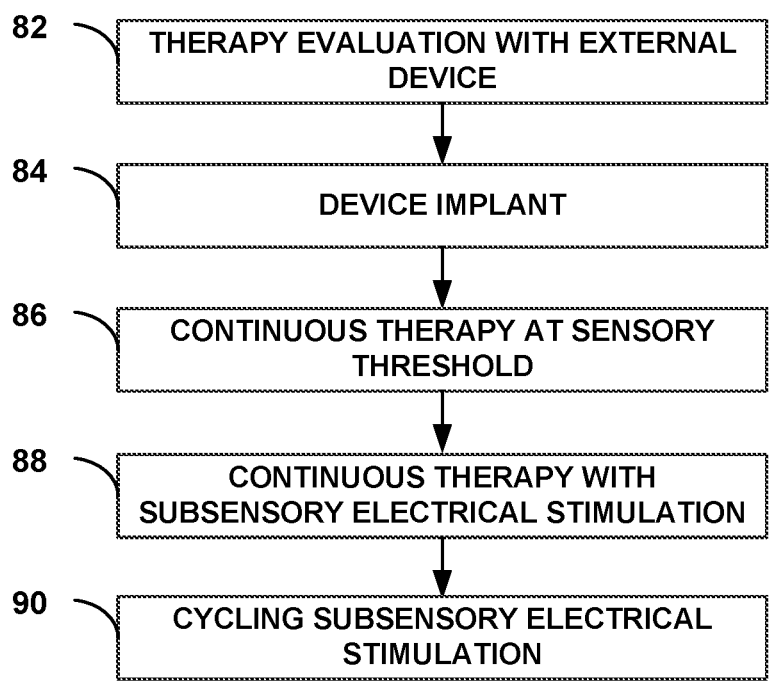
FIG. 5 is a flowchart illustrating example techniques related to controlling delivery of electrical stimulation therapy to a patient to help manage an incontinence condition of the patient.

FIG. 5 is a flowchart illustrating example techniques related to controlling delivery of electrical stimulation therapy to patient 14 to help manage an incontinence condition of patient 14. As described herein, the techniques illustrated in FIG. 5 may be employed using one or more components of systems 10A and 10B, which have been described above with respect to FIGS. 1-4. The example of FIG. 5 is provided merely as an example and should not be considered limiting. Steps of FIG. 5 may be skipped or performed out of order.

In FIG. 5, steps 82, 84, and 86 refer to steps in a therapy induction phase, and steps 88 and 90 refer to steps in a therapy maintenance phase. In the therapy induction phase, the clinician and patient 14 may determine the sensory threshold. In the therapy maintenance phase, patient 14 may be stimulated with subsensory electrical stimulation to treat incontinence.

As illustrated in FIG. 5, a clinician may review documentation that explains ways in which to set the therapy parameters for stimulating patient 14 to treat incontinence. The documentation may instruct the clinician to evaluate therapy with an external device (82). For example, the clinician may install an external medical device with leads that are subcutaneously inserted to be placed for incontinence. The lead placement may be for determining the sensory threshold. The documentation may instruct the clinician to titrate up or down the stimulation parameters until the clinician determines the sensory threshold. For example, the documentation may instruct the clinician to ask patient 14 if he/she is perceiving the electrical stimulation, or if the clinician can see or an accelerometer or other sensor can sense motor movement, or if there is an electrical signal that is generated and electrically sensed. In other words, the clinician may determine the sensory threshold (e.g., minimum intensity where patient 14 feels the stimulation, where patient 14 has a motor response, or where patient 14 generates an electrical signal such as EMG signal or eCAP).

The documentation may instruct the clinician to evaluate therapy over a period of time (e.g., 7 days or 14 days). For example, the documentation may instruct the clinician to cause the external device to deliver in continuous mode (e.g., nonstop) at a particular amplitude, pulse width, and frequency such that the resulting stimulation intensity is equal to the sensory threshold. As one example, the documentation may instruct the clinician to set the pulse width to 210 micro-seconds and the frequency to 14 Hz and determine which electrode configuration results in the smallest amplitude for the sensory threshold. The resulting amplitude, with 210 micro-seconds and 14 Hz in this example, is the amplitude parameter for sensory threshold.

Patient 14 may be implanted with IMD 16 (84). In some examples, step 82 may be skipped, and patient 14 may be first implanted with IMD 16 and the therapy evaluation described above for step 82 may be performed after IMD 16 is implanted. After implantation, the documentation may instruct the clinician to deliver therapy in continuous mode to the patient at the sensory threshold (86). For example, the documentation may instruct the clinician to allow IMD 16 to deliver continuous therapy at the sensory threshold for a certain amount of time (e.g., 4-6 weeks). During this time, the clinician may ensure that electrical stimulation is effective.

In this way, the documentation may instruct the clinician to determine a first set of therapy parameters for electrical stimulation at a sensory threshold. As described, an acute physiological occurs in patient 14 in response to the electrical stimulation at the sensory threshold. The documentation may instruct the clinician to determine that electrical stimulation at the sensory threshold results in effective incontinence therapy.

After the time period, the clinician, programmer 24, or IMD 16 may determine the therapy parameters for the subsensory electrical stimulation, as described above. IMD 16 may deliver continuous therapy with subsensory electrical stimulation (88). In some examples, the delivery of continuous therapy with subsensory electrical stimulation may be skipped.

The documentation may instruct the clinician to cause IMD 16 to deliver cycling subsensory electrical stimulation (90). As part of the cycling subsensory electrical stimulation, during a first time period (e.g., 6 weeks to 3 months), IMD 16 may deliver subsensory electrical stimulation with a certain on time (e.g., on-cycle) and certain off time (e.g., off-cycle) over the entire day. Then during a second time period, after the first time period, such as after 3 months, IMD 16 may deliver subsensory electrical stimulation with a certain on time and certain off time over a part of the day.

In one or more examples, during the maintenance phase, it may be possible that patient 14 chooses to revert back to stimulation at the sensory threshold. For such cases, it may be possible for patient 14, through programmer 24, to revert back to stimulation at the sensory threshold (e.g., restore therapy to full dose settings). There may be a button on programmer 24 that allows patient 14 to revert back to stimulation at the sensory threshold, or patient 14 may increase the amplitude, pulse width, and/or frequency to revert back to stimulation at the sensory threshold. Also, in some examples, stochastic stimulation and closed loop stimulation may be used to further improve the therapeutic effectiveness of the subsensory electrical stimulation.

There may be various ways in which memory 56 of IMD 16 may store the parameters for the subsensory electrical stimulation. As one example, the documentation may instruct the clinician to program IMD 16 with the set of therapy parameters for the subsensory electrical stimulation and cause IMD 16 to deliver the subsensory electrical stimulation based on the programmed set of therapy parameters. As another example, the documentation may instruct the clinician to program IMD 16 with the set of therapy parameters for sensory threshold, and IMD 16 may be configured to determine the set of therapy parameters for the subsensory electrical threshold based on the set of therapy parameters for the sensory threshold. The documentation may instruct the clinician to cause IMD 16 to deliver the subsensory electrical stimulation based on determined set of therapy parameters for the subsensory electrical stimulation. As another example, the documentation may instruct the clinician to program programmer 24 with the set of therapy parameters for the sensory threshold. Programmer 24 may be configured to determine the set of therapy parameters for the subsensory electrical stimulation based on the set of therapy parameters for the sensory threshold. The documentation may instruct the clinician to cause IMD 16 to deliver the subsensory electrical stimulation based on the determined set of therapy parameters for the subsensory electrical stimulation. In some examples, the techniques may be delivering subsensory electrical stimulation without first providing continuous therapy at the sensory threshold.

Figure 6:
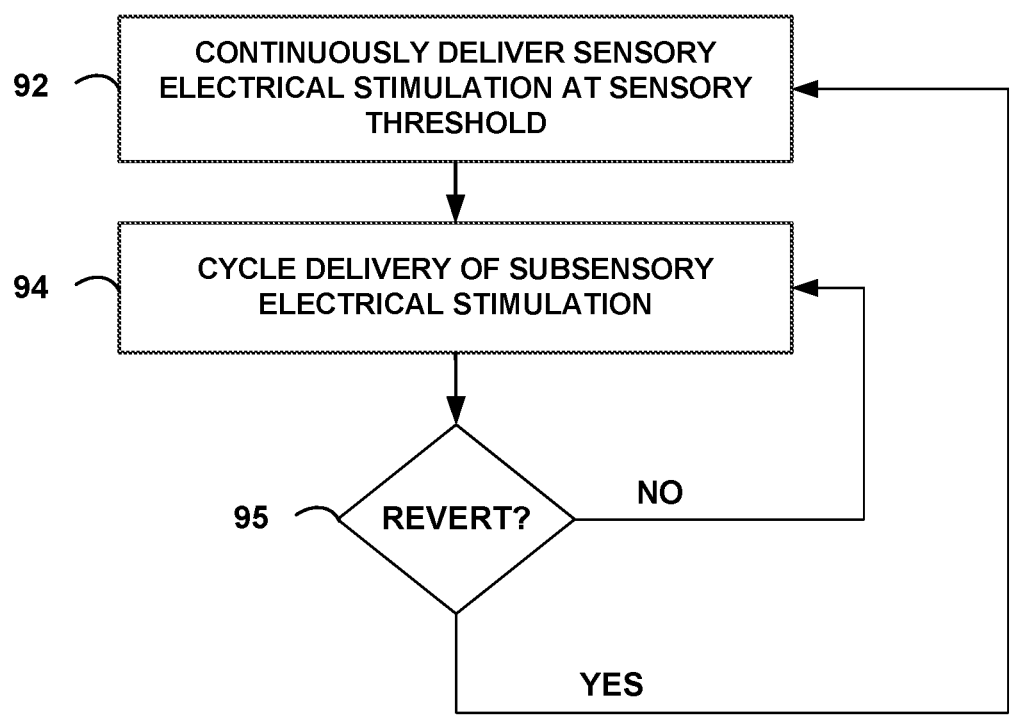
FIG. 6 is another flowchart illustrating example techniques related to controlling delivery of electrical stimulation therapy to patient to help manage an incontinence condition of patient.

FIG. 6 is another flowchart illustrating example techniques related to controlling delivery of electrical stimulation therapy to patient 14 to help manage an incontinence condition of patient 14. In one or more examples, memory 56 may be configured to store a first set of therapy parameters for delivery of sensory electrical stimulation at a sensory threshold during a therapy induction phase and a second set of therapy parameters for delivery of subsensory electrical stimulation during a therapy maintenance phase As illustrated in FIG. 6, IMD 16 (e.g., via therapy delivery circuitry 52) may continuously deliver the sensory electrical stimulation at the sensory threshold to patient 14 based on the first set of therapy parameters during the therapy induction phase (92). The delivery of the sensory electrical stimulation at the sensory threshold results in a therapeutic effect for incontinence therapy, and the therapy induction phase may include at least four weeks (although fewer weeks are possible) after implantation of IMD 16 within patient 14. Patient 14 perceives delivery of the sensory electrical stimulation at the sensory threshold. As one example, the first set of therapy parameters comprises a minimum current or voltage amplitude at which the patient perceives the sensory electrical stimulation, a pulse width of approximately 60 μs to 210 μs, and a frequency of approximately 5 Hz to 25 Hz. The minimum current or voltage amplitude at which the patient perceives the sensory electrical stimulation may be the sensory threshold.

IMD 16 (e.g., via therapy delivery circuitry 52) may cycle delivery of the subsensory electrical stimulation to patient 14 (94). For example, therapy delivery circuitry 52 may cycle delivery of the subsensory electrical stimulation to patient 14, between an on-cycle and an off-cycle, according to a cycle ratio of between about 2% and 50%, based on the second set of therapy parameters during the therapy maintenance phase. The subsensory electrical stimulation may have a stimulation intensity in range of less than 50% to approximately 80% of the stimulation intensity at the sensory threshold. In some examples, the therapy maintenance phase immediately follows the therapy induction phase, and delivery of the subsensory electrical stimulation results in the therapeutic effect for the incontinence therapy. Patient 14 may not perceive delivery of the subsensory electrical stimulation.

The second set of therapy parameters comprises a current or voltage amplitude that is in a range of 50% to 80% less than a minimum current or voltage amplitude at which the patient perceives the sensory electrical stimulation, a pulse width of approximately 60 μs to 210 μs, and a frequency of approximately 5 Hz to 25 Hz (e.g., 14 Hz). Therapy delivery circuitry 52 may be configured to deliver the subsensory electrical stimulation to at least one of a tibial or sacral nerve of patient 14.

In some examples, the on-cycle is approximately 8 hours and the off-cycle is approximately 16 hours. In some examples, the on-cycle is approximately 30 minutes and the off-cycle is approximately 30 minutes. In some examples, the on-cycle is approximately 1.5 hours and the off-cycle is approximately 1.5 hours. The stimulation intensity of the subsensory electrical stimulation may be less than or equal to 50% of the stimulation intensity at the sensory threshold.

As described, therapy delivery circuitry 52 may deliver subsensory electrical stimulation. Therapy delivery circuitry 52 may be configured to deliver the subsensory electrical stimulation based on the stored set of therapy parameters to provide immediate therapeutic effect caused by the ongoing delivery of the subsensory electrical stimulation to address incontinence. For instance, the delivery of the subsensory electrical stimulation may cause the therapeutic effect immediately rather than patient 14 experiencing the therapeutic effect after delivery of the subsensory electrical stimulation. Although the above example is described with respect to cycling, the example techniques are not limited to cycling. For instance, the delivery of the subsensory electrical stimulation (whether cycling or not) may provide immediate therapeutic effect caused by the ongoing delivery of the subsensory electrical stimulation to address incontinence at a desired level. Again, the delivery of the subsensory electrical stimulation may provide immediate therapy that addresses the incontinence at a desired level, rather than there being a delay in when patient 14 experiences the desired level of therapeutic effect.

Processing circuitry 50 may determine whether to revert back to continuous delivery of sensory electrical stimulation based on a patient request (95). If there is patient request to revert (YES of 95), processing circuitry 50 may cause therapy delivery circuitry 52 to, during the therapy maintenance phase, revert to continuous delivery of the sensory electrical stimulation at the sensory threshold to the patient based on the first set of therapy parameters in response to the patient request. If there is no patient request to revert (NO of 95), processing circuitry 50 may cause therapy delivery circuitry to cycle delivery of subsensory electrical stimulation.

Figure 7:
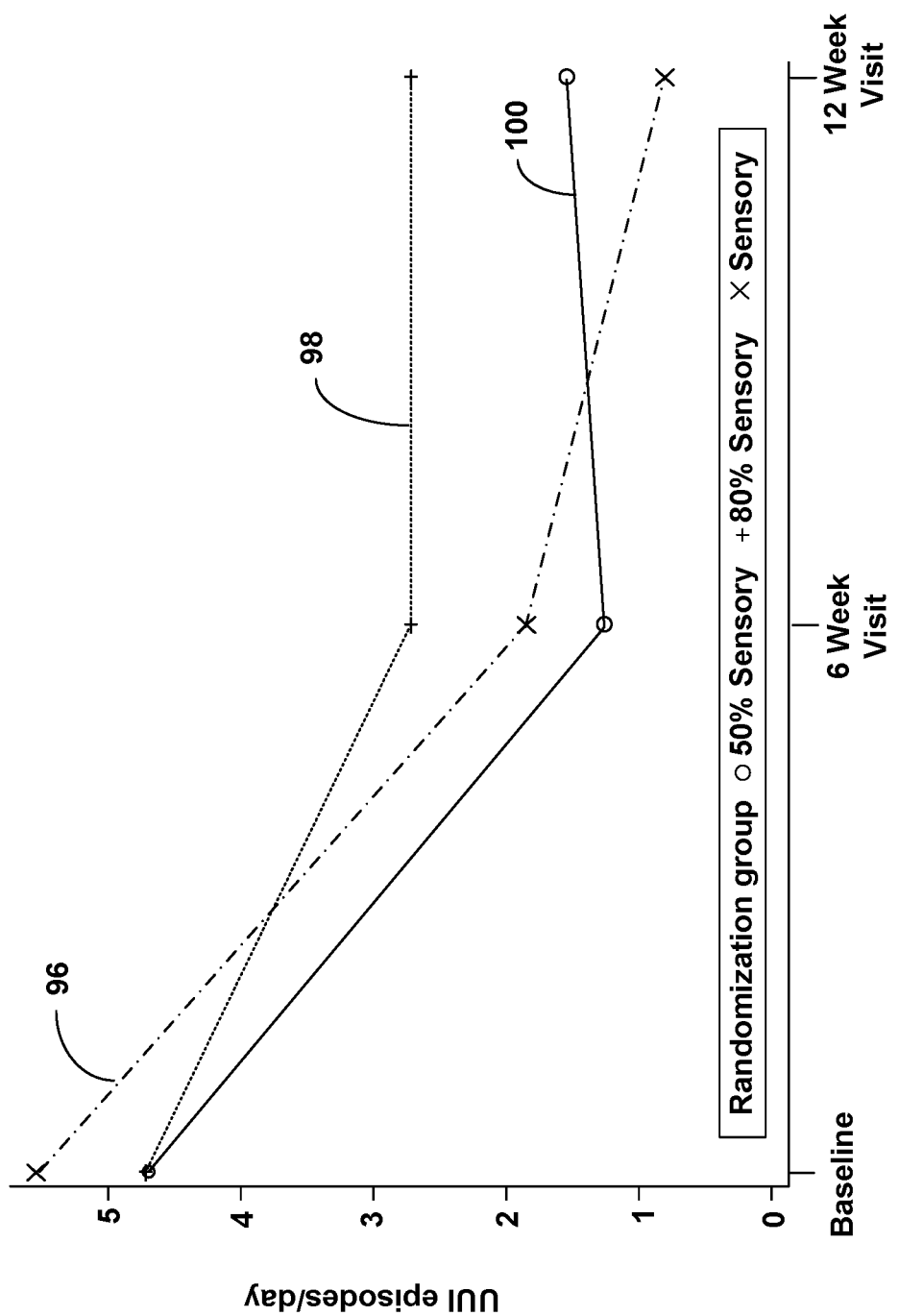
FIG. 7 is a graph illustrating interim results of therapy from subsensory electrical stimulation.

FIG. 7 is a graph illustrating interim results of therapy from subsensory electrical stimulation. The x-axis of FIG. 7 indicates the number of weeks from initial setting of stimulation intensity. The y-axis of FIG. 7 indicates the number of urge urinary incontinent (UUI) episodes (e.g., leakage episodes) per day. Line 96 reflects the number of urinary incontinent episodes per day over time for when patients received therapy at the sensory threshold. Line 98 reflects the number of urinary incontinent episodes per day over time for when patients received therapy with subsensory electrical stimulation (e.g., 80% of the sensory threshold). Line 100 reflects the number of urinary incontinent episodes per day over time for when patients received therapy with subsensory electrical stimulation (e.g., 50% of the sensory threshold).

The results illustrated in FIG. 7 are generated by stimulating three groups. For each group, a clinician determined the sensory threshold. The first group (identified by line 96) then received therapy at the sensory threshold. For the second group (identified by line 98), the clinician reduced the amplitude to 80% of the amplitude at the sensory threshold. For the third group (identified by line 100), the clinician reduced the amplitude to 50% of the amplitude of the sensory threshold. The other parameters (e.g., pulse width and frequency) were not changed. Lines 96, 98, and 100 show the mean results for each group.

As illustrated, initially delivering therapy at the sensory threshold provides worse results (e.g., more incontinence episodes) at the baseline, as shown by line 96, as compared to the 80% of sensory threshold, as shown by line 98, or 50% of sensory threshold, as shown by line 100. Baseline refers to UUI episodes/day prior to initiation of therapy. The 1, 6 and 12 week timepoints then indicate reduction of UUI episodes from baseline values at those times after initiating therapy at sensory threshold, 80% sensory threshold, and 50% sensory threshold.

However, overtime, such as at 12 weeks, FIG. 7 shows that therapy at the sensory threshold (e.g., line 96) had fewer number of incontinence episodes per day as compared to 50% of sensory threshold (e.g., line 100) and 80% of sensory threshold (e.g., line 98). FIG. 7 does not illustrate the variability in the results of the groups. In some cases, when the variability of the results for each group, rather than just the mean, is accounted for, the results may show that there is very little change in the therapeutic effectiveness of the therapy delivery between 50% to 80% amplitude, as compared to therapeutic effectiveness of therapy at the sensory threshold.

Figure 8:
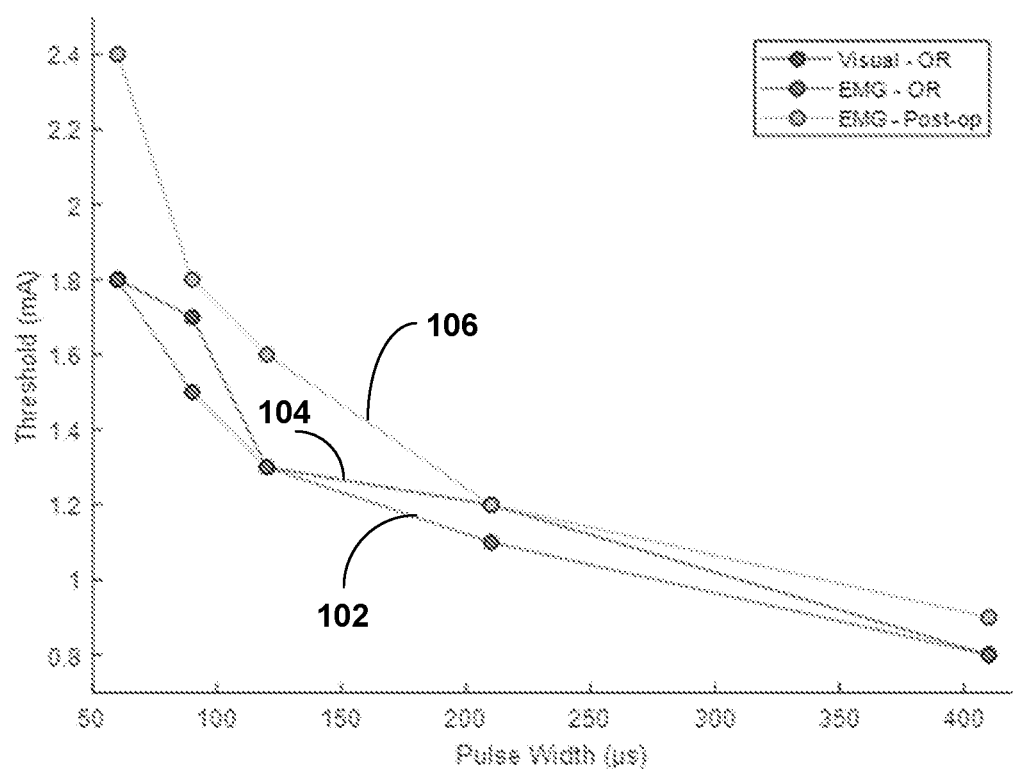
FIG. 8 is a graph illustrating an example of strength-duration curves that may be utilized to determine subsensory electrical stimulation parameters.

FIG. 8 is a graph illustrating an example of strength-duration curves that may be utilized to determine subsensory electrical stimulation parameters. The strength-duration curves of FIG. 8 illustrate amplitude of electrical stimulation relative to pulse width to generate an motor response from the patient (e.g., an EMG). Lines 102 and 104 are generated intra-operatively, and line 106 is generated post-operatively. In general, lines 102, 104, and 106 may be considered as illustrating parameters (e.g., amplitude and pulse width) for the motor threshold. In other words, when patient 14 is stimulated with an amplitude and corresponding pulse width from one of lines 102, 104, and 106, patient 14 may be considered as receiving electrical stimulation at the motor threshold.

For example, the surgeon may set a particular pulse width (e.g., approximately 50 micro-seconds to approximately 400 micro-seconds) and determine the amplitude at which the nerve is captured to provide effective therapy. There may be various ways in which the surgeon may determine that there is nerve capture. As one example, the patient may have a motor response to the stimulation, and an EMG signal may be measured. As another example of a motor response (e.g., which is an example of sensor threshold), the patient may have a physiological response (e.g., clenching of buttocks) to the stimulation that can be visually observed rather than measured with EMG.

Line 102 is generated intra-operatively. During the operation, the surgeon may set a particular pulse width and titrate the amplitude until there is an EMG signal. The surgeon may record the amplitude for the particular pulse width that generate the EMG signal. The surgeon may then change the pulse width and repeat. In this manner, the surgeon may generate line 102. In some examples, the surgeon may select a particular amplitude and titrate the pulse width until there is an EMG signal, record the pulse width for the particular amplitude, change the amplitude and repeat to generate line 102.

Line 104 is also generated intra-operatively. Rather than measuring EMG signal, line 104 is based on visible changes in the patient. For example, the surgeon may generate line 104 similar to line 102. However, rather than determining when there is an EMG, the surgeon may monitor the patient to determine when the buttocks of the patient clench. The surgeon may record the amplitude, for a given pulse width, or pulse width, for a given amplitude, at which the buttocks of the patient clenched to generate line 104.

Line 106 is generated post-operatively. The surgeon or clinician may generate line 106 similar to line 102 (e.g., using EMG signal) but post-operatively rather than intra-operatively. Although not shown, it may be possible to generate a line, like line 104, that is based on visually perceived changes in the patient in a post-operative setting.

In some examples, patient 14, the surgeon, and/or the clinician may utilize the examples of the strength-duration curves of FIG. 8 to determine the subsensory electrical stimulation parameters. For example, patient 14, the surgeon, and/or the clinician may determine the amplitude for a given pulse width (or vice-versa) that provides stimulation at the motor responses (e.g., which may be used as proxy for sensory threshold), using any one of lines 102, 104, and 106. As one example, using line 106, the clinician may determine that for 100 micro-second pulse width, the amplitude is 1.8 mA for electrical stimulation at the sensory threshold. To achieve 50% of sensory threshold stimulation (e.g., subsensory electrical stimulation having intensity that is 50% of the intensity of the sensory threshold), the clinician may reduce the amplitude of 1.8 mA by 50% (e.g., 0.9 mA).

In general, responses plotted in strength duration curves (e.g., of FIG. 8) are for motor responses, and could be used as a proxy for sensory threshold. For instance, intraoperatively the patient is anesthetized and cannot report sensation therefore an EMG-measured motor response could be used as a proxy for the sensory responses under the same stimulation conditions (e.g. pulse width and amplitude).

In some examples, processing circuitry 50 and/or processing circuitry 70 may be configured to determine the electrical stimulation parameters for the subsensory electrical stimulation. For example, memory 56 and/or memory 72 may store tables or line equations for one or more of lines 102, 104, and 106. Processing circuitry 50 and/or processing circuitry 70 may determine the amplitude for a given pulse width (or vice-versa) that results in stimulation at the sensory threshold based on the tables or line equations stored in memory 56 and/or memory 72. Processing circuitry 50 and/or processing circuitry 70 may scale the amplitude and/or pulse width to achieve the desired subsensory electrical stimulation (e.g., scale the amplitude or pulse width by 50% to achieve electrical stimulation having 50% intensity relative to sensory threshold).

FIGS. 9A-9E are graphs illustrating examples of an electromyography (EMG) signals for different pulse widths with stimulation at sensory threshold or above and subsensory electrical stimulation. In FIGS. 9A-9E, lines 108A-108E represent the EMG signal generated when electrical stimulation at the sensory threshold is delivered (e.g., which is based on being a proxy for motor response). Lines 110A-110E represent the EMG signal generated when subsensory electrical stimulation is delivered. For example, lines 110A-110E are generated by reducing the amplitude by 0.1 mA from the amplitude that was used to generate lines 108A-108E (e.g., if 0.8 mA is used to generate lines 108A-108E, then 0.7 mA is used to generate lines 110A-110E).

Figure 9A:
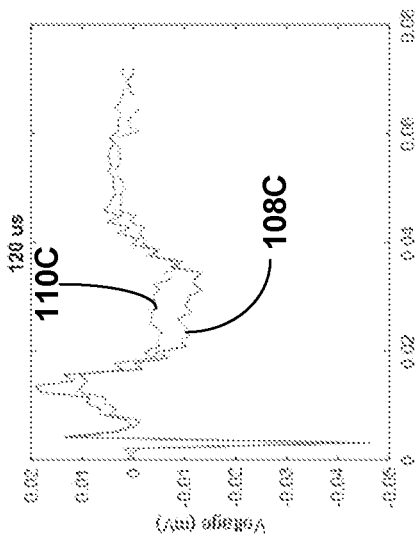
FIGS. 9A-9E are graphs illustrating examples of an electromyography (EMG) signals for different pulse widths with stimulation at sensory threshold or above and subsensory electrical stimulation.
Figure 9B:
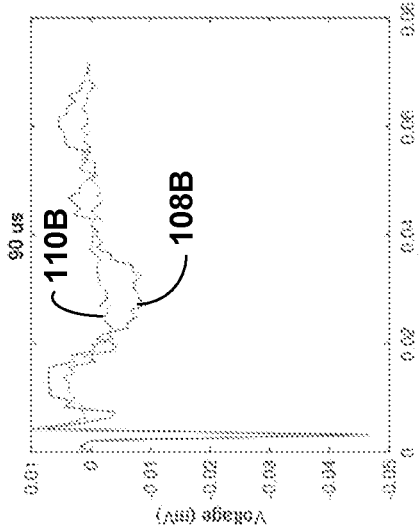
Figure 9C:
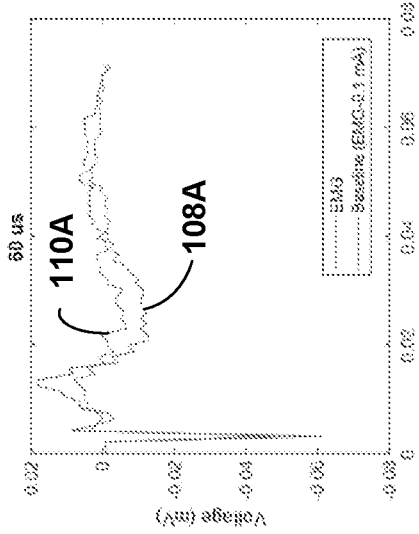
Figure 9D:
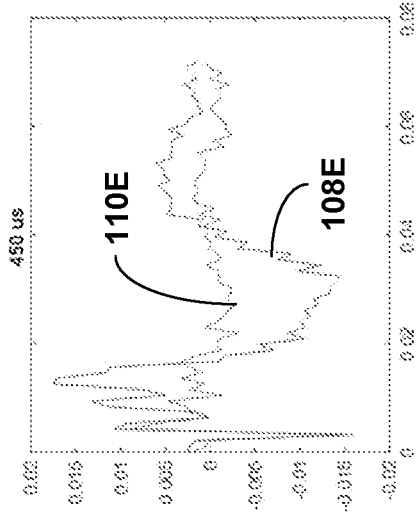
Figure 9E:
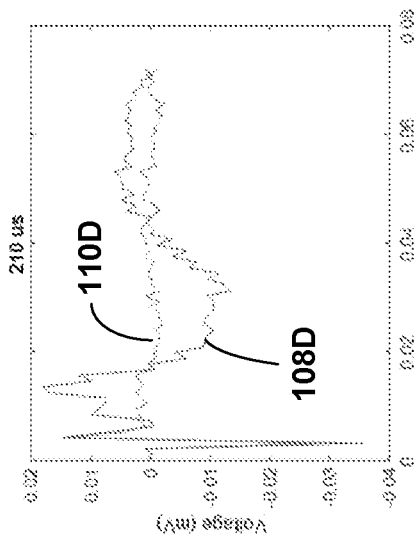

Each one of FIGS. 9A-9E are generated with different pulse widths. For instance, FIG. 9A is generated with pulse width of 60 micro-seconds, FIG. 9B is generated with pulse width of 90 micro-seconds, FIG. 9C is generated with pulse width of 120 micro-seconds, FIG. 9D is generated with pulse width of 210 micro-seconds, and FIG. 9E is generated with pulse width of 450 micro-seconds. In some examples, the pulse width of the subsensory electrical stimulation may be in the range of approximately 60 micro-seconds to approximately 450 micro-seconds.

The following provides additional results from subsensory electrical stimulation. The results were generated from a multicenter, randomized, single-blind feasibility study to explore the efficacy and quality of life under three different amplitude settings (subsensory amplitudes of 50% and 80% of sensory threshold and amplitude at the sensory threshold for respective patients). For example, the amplitude at the sensory threshold may be different for different patients, and therefore, the amplitude of the 50% and 80% of sensory threshold stimulation may be different for different patients. Efficacy was characterized by assessing change from baseline through twelve weeks in number of urge urinary incontinent (UUI) episodes and patient reported outcomes (e.g., qualitative information provided by the patients).

During programming, the subject's sensory threshold amplitude may be determined according to the following process: start stimulation at an amplitude of 0.05 volts (V) and increase the voltage amplitude in 0.05-0.1 V increments until the subject reports sensation. One example of sensory threshold may be the stimulation amplitude at which the subject perceives the first sensation of the stimulation in the perineum, perianal region, vaginal region, leg, toe or any location deemed appropriate while in a seated position.

Subjects were randomized to one of the three amplitude settings: 50% of sensory threshold, 80% of sensory threshold, and sensory threshold. One objective was to explore and characterize the reduction in number of UUI episodes under each amplitude setting from baseline.

Change in UUI episodes per day (e.g., over 24 hour period) from baseline to 12 weeks is summarized in Table 1 and the change in UUI episodes per day from baseline to 6 weeks is summarized in Table 2. In Table 1, the change from baseline to 12 weeks is −3.1 UUI episodes per day (95% CI (confidence interval): −4.7 to −1.5) for the 50% of Sensory Threshold group, −2.9 UUI episodes/day (95% CI: −4.7 to −1.2) for 80% of Sensory Threshold group, and −3.6 UUI episodes/day (95% CI: −5.6 to −1.6) for the Sensory Threshold group. UUI episodes were included in the calculation irrespective of urgency status.

TABLE 1

Change in UUI episodes/day from Baseline to 12 Weeks, Primary Analysis (Complete Case Subject Set)

| Measure | 50% of Sensory Threshold Mean ± SD (N) Median [Min, Max] 95% CI | 80% of Sensory Threshold Mean ± SD (N) Median [Min, Max] 95% CI | Sensory Threshold Mean ± SD (N) Median [Min, Max] 95% CI |
|---|---|---|---|
| Baseline | 4.7 ± 3.1 (14) 3.2 [1.7, 11.7] 3.0, 6.5 | 5.3 ± 3.1 (13) 4.3 [2.7, 14.3] 3.4, 7.2 | 5.3 ± 5.1 (11) 3.7 [1.7, 20.0] 1.9, 8.7 |
| 12 Weeks | 1.6 ± 2.9 (14) 0.3 [0.0, 10.0] −0.0, 3.3 | 2.4 ± 3.0 (13) 1.0 [0.0, 9.7] 0.5, 4.2 | 1.7 ± 2.5 (11) 1.0 [0.0, 8.3] 0.0, 3.4 |
| Change from Baseline to 12 weeks | −3.1 ± 2.7 (14) −2.3 [−7.7, 2.0] −4.7, −1.5 | −2.9 ± 2.9 (13) −3.0 [−8.0, 4.7] −4.7, −1.2 | −3.6 ± 3.0 (11) −3.3 [−11.7, −0.7] −5.6, −1.6 |
| Percent Change from Baseline to 12 weeks | −69.8 ± 47.8 (14) −91.3 [−100, 60.0] −97.4, −42.2 | −60.0 ± 51.2 (13) −70.0 [−100, 93.3] −90.9, −29.1 | −72.7 ± 28.2 (11) −83.3 [−100, −30.8] −91.6, −53.8 |

TABLE 2

Change in UUI episodes/day from Baseline to 6 Weeks, Primary Analysis (Complete Case Subject Set)

| Measure | 50% of Sensory Threshold Mean ± SD (N) Median [Min, Max] 95% CI | 80% of Sensory Threshold Mean ± SD (N) Median [Min, Max] 95% CI | Sensory Threshold Mean ± SD (N) Median [Min, Max] 95% CI |
|---|---|---|---|
| Baseline | 4.4 ± 2.9 (17) 3.0 [1.3, 11.7] 2.9, 5.9 | 5.3 ± 3.1 (13) 4.3 [2.7, 14.3] 3.4, 7.2 | 4.9 ± 4.8 (13) 3.7 [1.3, 20.0] 2.0, 7.9 |
| 6 Weeks | 1.3 ± 2.0 (17) 0.3 [0.0, 6.7] 0.3, 2.3 | 2.4 ± 3.6 (13) 0.3 [0.0, 10.7] 0.2, 4.6 | 1.5 ± 2.5 (13) 0.7 [0.0, 9.3] −0.0, 3.0 |
| Change from Baseline to 6 weeks | −3.1 ± 2.5 (17) −2.3 [−7.7, 1.3] −4.4, −1.8 | −2.9 ± 2.6 (13) −3.7 [−6.0, 4.3] −4.5, −1.3 | −3.5 ± 2.5 (13) −3.3 [−10.7, −1.3] −5.0, −1.9 |
| Percent Change from Baseline to 6 weeks | −70.7 ± 41.3 (17) −87.5 [−100, 44.4] −92.0, −49.5 | −61.8 ± 56.3 (13) −93.8 [−100, 86.7] −95.8, −27.7 | −78.2 ± 17.8 (13) −82.4 [−100, −50.0] −88.9, −67.4 |

Figure 10:
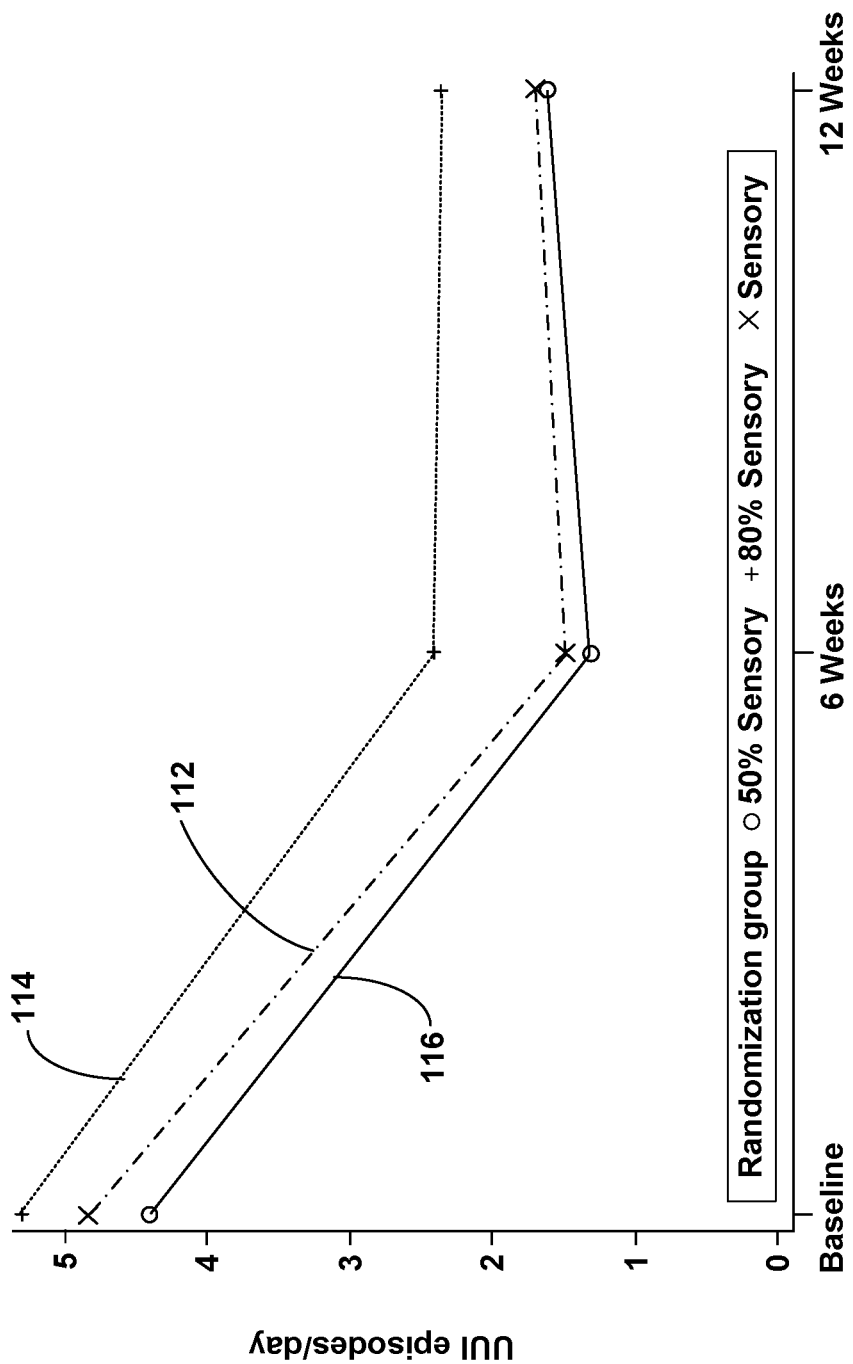
FIG. 10 is a graph illustrating results of therapy from subsensory electrical stimulation.

FIG. 10 is a graph illustrating results of therapy from subsensory electrical stimulation. In particular, FIG. 10 illustrates the results of the therapy from subsensory electrical stimulation from the patient testing described above and shown in Tables 1 and 2. For instance, FIG. 7 illustrates one example of the results of therapy from subsensory electrical stimulation, and FIG. 10 illustrates another example of the results for therapy from subsensory electrical stimulation.

Similar to FIG. 7, the x-axis of FIG. 10 indicates the number of weeks from initial setting of stimulation intensity, and the y-axis of FIG. 10 indicates the number of urge urinary incontinent (UUI) episodes (e.g., leakage episodes) per day. Line 112 reflects the number of urinary incontinent episodes per day over time for when patients received therapy at the sensory threshold. Line 114 reflects the number of urinary incontinent episodes per day over time for when patients received therapy with subsensory electrical stimulation at 80% of the sensory threshold. Line 116 reflects the number of urinary incontinent episodes per day over time for when patients received therapy with subsensory electrical stimulation at 50% of the sensory threshold.

As described above, the results illustrated in FIG. 10, like FIG. 7, are generated by stimulating three groups of patients. For each group, a clinician determined the sensory threshold. The first group (identified by line 112) then received therapy at the sensory threshold. For the second group (identified by line 114), the clinician delivered the electrical stimulation at 80% of the amplitude at the sensory threshold. For the third group (identified by line 116), the clinician delivered the electrical stimulation at 50% of the amplitude of the sensory threshold. The other parameters (e.g., pulse width and frequency) were not changed. Lines 112, 114, and 116 show the mean results for each group.

For the therapy, the pulse width was fixed at 210 microseconds and the frequency was fixed at 14 Hz. However, pulse width of 210 microseconds and frequency of 14 Hz is one example and should not be considered limiting. The pulse width may be 60 microseconds to 210 microseconds, and the pulse width may be 5 Hz to 25 Hz. Table 3 illustrates examples of sensory thresholds.

TABLE 3

Sensory Thresholds

| | By group | | | |
|---|---|---|---|---|
| Sensory thresholds | 50% of Sensory Threshold Mean ± SD (N) Median [Min, Max] | 80% of Sensory Threshold Mean ± SD (N) Median [Min, Max] | Sensory Threshold Mean ± SD (N) Median [Min, Max] | Total Mean ± SD (N) Median [Min, Max] |
| Seated: Lowest threshold of sensory response (V) | 1.1 ± 0.8 (18) 0.8 [0.4, 3.2] | 0.8 ± 0.4 (13) 0.8 [0.4, 1.9] 3.4, 7.2 | 0.8 ± 0.3 (13) 0.7 [0.5, 1.5] | 0.9 ± 0.6 (44) 0.7 [0.4, 3.2] |

As illustrated, delivering therapy at 50% of sensory threshold resulted in the fewest incontinence episodes, as shown by line 116, as compared to delivering therapy at the sensory threshold, as shown by line 112, and delivering therapy at 80% of sensory threshold, as shown by line 114. For instance, at baseline (e.g., prior to delivery of therapy), after 6 weeks, and after 12 weeks, the patients experienced the fewest incontinence episodes when the therapy was delivered at 50% of sensory threshold. In the results shown in FIG. 10, delivering therapy at 80% of sensory threshold had the most incontinence episodes.

Table 4 is an example of cycle ratio, on- and off-cycles, and stimulation intensity that IMD 16 may be deliver to provide immediate therapeutic effect caused by the ongoing delivery of the subsensory electrical stimulation to address incontinence (e.g., address incontinence at the desired level of therapeutic response). It should be understood that the on-cycle and off-cycle for a cycle ratio is provided as one example in Table 4. Other on-cycles and off-cycles may be used to achieve the same cycle ratio. Also, the cycle ratio and the stimulation intensity may be within a range of cycle ratios and stimulation intensity, and are not limited to the specific cycle ratio and stimulation intensity in Table 4.

TABLE 4

| Cycle Ratio | On-Cycle | Off-Cycle | Stimulation Intensity |
|---|---|---|---|
| 2% | 30 minutes | 23.5 hours | 95% |
| 2% | 30 minutes | 23.5 hours | 80% |
| 2% | 30 minutes | 23.5 hours | 50% |
| 33% | 8 hours | 16 hours | 95% |
| 33% | 8 hours | 16 hours | 50% |
| 50% | 1.5 hours | 1.5 hours | 50% |
| 50% | 30 minutes | 30 minutes | 50% |

While the techniques described above are primarily described as being performed by processing circuitry 50 of IMD 16 or processing circuitry 70 of programmer 24, in other examples, one or more other processors may perform any part of the techniques described herein alone or in addition to processing circuitry 50 or processing circuitry 70. Thus, reference to "processing circuitry" may refer to "one or more processing circuitries." Likewise, "one or more processing circuitries" may refer to single or multiple processing circuitries in different examples.

The following describes one or more examples techniques. The example techniques may be performed separately or in any combination.

Example 1. A system comprising a memory configured to store a first set of therapy parameters for delivery of sensory electrical stimulation at a sensory threshold during a therapy induction phase and a second set of therapy parameters for delivery of subsensory electrical stimulation during a therapy maintenance phase and therapy delivery circuitry configured to continuously deliver the sensory electrical stimulation at the sensory threshold to a patient based on the first set of therapy parameters during the therapy induction phase, wherein delivery of the sensory electrical stimulation at the sensory threshold results in a therapeutic effect for incontinence therapy, wherein the therapy induction phase includes at least four weeks after implantation of an implantable medical device (IMD) within the patient, and wherein the patient perceives delivery of the sensory electrical stimulation at the sensory threshold, and cycle delivery of the subsensory electrical stimulation to the patient, between an on-cycle and an off-cycle, according to a cycle ratio of between about 2% and 50%, based on the second set of therapy parameters during the therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

Example 2. The system of example 1, wherein the on-cycle is approximately 8 hours and the off-cycle is approximately 16 hours.

Example 3. The system of example 1, wherein the on-cycle is approximately 30 minutes and the off-cycle is approximately 30 minutes.

Example 4. The system of example 1, wherein the on-cycle is approximately 1.5 hours and the off-cycle is approximately 1.5 hours.

Example 5. The system of any of examples 1-4, wherein the stimulation intensity of the subsensory electrical stimulation is less than or equal to 50% of the stimulation intensity at the sensory threshold.

Example 6. The system of any of examples 1-5, wherein, during the therapy maintenance phase, the therapy delivery circuitry is configured to revert to continuous delivery of the sensory electrical stimulation at the sensory threshold to the patient based on the first set of therapy parameters in response to a patient request.

Example 7. The system of any of examples 1-6, wherein the first set of therapy parameters comprises a minimum current or voltage amplitude at which the patient perceives the sensory electrical stimulation, a pulse width of approximately 60 µs to 210 µs, and a frequency of approximately 5 to 25 Hz, wherein the minimum current or voltage amplitude at which the patient perceives the sensory electrical stimulation is the sensory threshold.

Example 8. The system of any of examples 1-7, wherein the second set of therapy parameters comprises a current or voltage amplitude that is in a range of 50% to 80% less than a minimum current or voltage amplitude at which the patient perceives the sensory electrical stimulation, a pulse width of approximately 60 µs to 210 µs, and a frequency of approximately 5 to 25 Hz.

Example 9. The system of any of examples 1-8, wherein the therapy delivery circuitry is configured to deliver the subsensory electrical stimulation to at least one of a tibial or sacral nerve of the patient.

Example 10. The system of any of examples 1-9, wherein the IMD comprises the therapy delivery circuitry, and wherein at least one of a programmer or the IMD comprises the memory.

Example 11. A method comprising continuously delivering, with an implantable medical device (IMD), sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold, and cycling, with the IMD, delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

Example 12. The method of example 11, wherein the on-cycle is approximately 8 hours and the off-cycle is approximately 16 hours.

Example 13. The method of example 11, wherein the on-cycle is approximately 30 minutes and the off-cycle is approximately 30 minutes.

Example 14. The method of example 11, wherein the on-cycle is approximately 1.5 hours and the off-cycle is approximately 1.5 hours.

Example 15. The method of any of examples 11-14, wherein the stimulation intensity of the subsensory electrical stimulation is less than or equal to 50% of the stimulation intensity at the sensory threshold.

Example 16. The method of any of examples 11-15, further comprising, during the therapy maintenance phase, reverting to continuous delivery of the sensory electrical stimulation at the sensory threshold to the patient based on the first set of therapy parameters in response to a patient request.

Example 17. The method of any of examples 11-16, wherein the first set of therapy parameters comprises a minimum current or voltage amplitude at which the patient perceives the sensory electrical stimulation, a pulse width of approximately 60 µs to 210 µs, and a frequency of approximately 5 to 25 Hz, wherein the minimum current or voltage amplitude at which the patient perceives the sensory electrical stimulation is the sensory threshold.

Example 18. The method of any of examples 11-17, wherein the second set of therapy parameters comprises a current or voltage amplitude that is in a range of 50% to 80% less than a minimum current or voltage amplitude at which the patient perceives the sensory electrical stimulation, a pulse width of approximately 60 µs to 210 µs, and a frequency of approximately 5 to 25 Hz.

Example 19. The method of any of examples 11-18, wherein cycling delivery of the subsensory electrical stimulation to the patient comprises cycling delivery of the subsensory electrical stimulation to at least one of a tibial or sacral nerve of the patient.

Example 20. A computer-readable storage medium storing instructions thereon that when executed cause one or more processors of an implantable medical device (IMD) to continuously deliver sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold, and cycle delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

Example 21. The computer-readable storage medium of example 20, wherein the on-cycle and the off-cycle comprise one of the following pairs: (1) the on-cycle is approximately 8 hours and the off-cycle is approximately 16 hours, (2) the on-cycle is approximately 30 minutes and the off-cycle is approximately 30 minutes, or (3) the on-cycle is approximately 1.5 hours and the off-cycle is approximately 1.5 hours.

Example 22. The computer-readable storage medium of any of examples 20 and 21, wherein the stimulation intensity of the subsensory electrical stimulation is less than or equal to 50% of the stimulation intensity at the sensory threshold.

Example 23. The computer-readable storage medium of any of examples 20-22, further comprising instructions that cause the one or more processors to during the therapy maintenance phase, revert to continuous delivery of the sensory electrical stimulation at the sensory threshold to the patient based on the first set of therapy parameters in response to a patient request.

Example 24. A implantable medical device (IMD) comprising a memory configured to store a set of therapy parameters for subsensory electrical stimulation of a patient and therapy delivery circuitry configured to deliver the subsensory electrical stimulation to at least one of a sacral nerve or tibial nerve based on the stored set of therapy parameters to provide immediate therapeutic effect caused by the ongoing delivery of the subsensory electrical stimulation to address incontinence, wherein a stimulation intensity of the subsensory electrical stimulation is less than 80% of a stimulation intensity at a sensory threshold, and wherein the patient does not perceive delivery of the subsensory electrical stimulation and perceives delivery of stimulation at the sensory threshold.

Example 25. The IMD of example 24, wherein to deliver the subsensory electrical stimulation, the therapy delivery circuitry is configured to cycle delivery of the subsensory electrical stimulation to the patient, between an on-cycle and an off-cycle, according to a cycle ratio of between about 2% and 50%.

Example 26. The IMD of example 25, wherein the on-cycle and the off-cycle comprise one of the following pairs: (1) the on-cycle is approximately 8 hours and the off-cycle is approximately 16 hours, (2) the on-cycle is approximately 30 minutes and the off-cycle is approximately 30 minutes, or (3) the on-cycle is approximately 1.5 hours and the off-cycle is approximately 1.5 hours.

Example 27. The IMD of any of examples 24-26, wherein the stimulation intensity of the subsensory electrical stimulation is less than or equal to 50% of the stimulation intensity at the sensory threshold.

For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein. The parameters associated with the cycle settings described above may be stored in memory of the IMD or in memory of another device, and used by processing circuitry 50 to control delivery of the electrical stimulation.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A system comprising:
a memory configured to store a first set of therapy parameters for delivery of sensory electrical stimulation at a sensory threshold during a therapy induction phase and a second set of therapy parameters for delivery of subsensory electrical stimulation during a therapy maintenance phase; and
therapy delivery circuitry configured to:
continuously deliver the sensory electrical stimulation at the sensory threshold to a patient based on the first set of therapy parameters during the therapy induction phase, wherein delivery of the sensory electrical stimulation at the sensory threshold results in a therapeutic effect for incontinence therapy, wherein the therapy induction phase includes at least four weeks after implantation of an implantable medical device (IMD) within the patient, and wherein the patient perceives delivery of the sensory electrical stimulation at the sensory threshold; and
cycle delivery of the subsensory electrical stimulation to the patient, between an on-cycle and an off-cycle, according to a cycle ratio of between about 2% and 50%, based on the second set of therapy parameters during the therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

2. The system of claim 1, wherein the on-cycle is approximately 8 hours and the off-cycle is approximately 16 hours.

3. The system of claim 1, wherein the on-cycle is approximately 30 minutes and the off-cycle is approximately 30 minutes.

4. The system of claim 1, wherein the on-cycle is approximately 1.5 hours and the off-cycle is approximately 1.5 hours.

5. The system of claim 1, wherein the stimulation intensity of the subsensory electrical stimulation is less than or equal to 50% of the stimulation intensity at the sensory threshold.

6. The system of claim 1, wherein, during the therapy maintenance phase, the therapy delivery circuitry is configured to revert to continuous delivery of the sensory electrical stimulation at the sensory threshold to the patient based on the first set of therapy parameters in response to a patient request.

7. The system of claim 1, wherein the first set of therapy parameters comprises a minimum current or voltage amplitude at which the patient perceives the sensory electrical stimulation, a pulse width of approximately 60 µs to 210 µs, and a frequency of approximately 5 to 25 Hz, wherein the minimum current or voltage amplitude at which the patient perceives the sensory electrical stimulation is the sensory threshold.

8. The system of claim 1, wherein the second set of therapy parameters comprises a current or voltage amplitude that is in a range of 50% to 80% less than a minimum current or voltage amplitude at which the patient perceives the sensory electrical stimulation, a pulse width of approximately 60 µs to 210 µs, and a frequency of approximately 5 to 25 Hz.

9. The system of claim 1, wherein the therapy delivery circuitry is configured to deliver the subsensory electrical stimulation to at least one of a tibial or sacral nerve of the patient.

10. The system of claim 1, wherein the IMD comprises the therapy delivery circuitry, and wherein at least one of a programmer or the IMD comprises the memory.

11. A method comprising:
continuously delivering, with an implantable medical device (IMD), sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold; and
cycling, with the IMD, delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

12. The method of claim 11, wherein the on-cycle is approximately 8 hours and the off-cycle is approximately 16 hours.

13. The method of claim 11, wherein the on-cycle is approximately 30 minutes and the off-cycle is approximately 30 minutes.

14. The method of claim 11, wherein the on-cycle is approximately 1.5 hours and the off-cycle is approximately 1.5 hours.

15. The method of claim 11, wherein the stimulation intensity of the subsensory electrical stimulation is less than or equal to 50% of the stimulation intensity at the sensory threshold.

16. The method of claim 11, further comprising, during the therapy maintenance phase, reverting to continuous delivery of the sensory electrical stimulation at the sensory threshold to the patient based on the first set of therapy parameters in response to a patient request.

17. The method of claim 11, wherein the first set of therapy parameters comprises a minimum current or voltage amplitude at which the patient perceives the sensory electrical stimulation, a pulse width of approximately 60 µs to 210 µs, and a frequency of approximately 5 to 25 Hz, wherein the minimum current or voltage amplitude at which the patient perceives the sensory electrical stimulation is the sensory threshold.

18. The method of claim 11, wherein the second set of therapy parameters comprises a current or voltage amplitude that is in a range of 50% to 80% less than a minimum current or voltage amplitude at which the patient perceives the sensory electrical stimulation, a pulse width of approximately 60 µs to 210 µs, and a frequency of approximately 5 to 25 Hz.

19. The method of claim 11, wherein cycling delivery of the subsensory electrical stimulation to the patient comprises cycling delivery of the subsensory electrical stimulation to at least one of a tibial or sacral nerve of the patient.

20. A computer-readable storage medium storing instructions thereon that when executed cause one or more processors of an implantable medical device (IMD) to:
continuously deliver sensory electrical stimulation at a sensory threshold to a patient based on a first set of therapy parameters during a therapy induction phase, wherein delivery of the sensory electrical stimulation at the sensory threshold results in a therapeutic effect for incontinence therapy, wherein the therapy induction phase includes at least four weeks after implantation of the IMD within the patient, and wherein the patient perceives delivery of the sensory electrical stimulation at the sensory threshold; and
cycle delivery of the subsensory electrical stimulation to the patient, between an on-cycle and an off-cycle, according to a cycle ratio of between about 2% and 50%, based on a second set of therapy parameters during a therapy maintenance phase, the subsensory electrical stimulation having a stimulation intensity less than 80% of the stimulation intensity at the sensory threshold, wherein the therapy maintenance phase immediately follows the therapy induction phase, wherein delivery of the subsensory electrical stimulation results in the therapeutic effect for the incontinence therapy, and wherein the patient does not perceive delivery of the subsensory electrical stimulation.

21. The computer-readable storage medium of claim 20, wherein the on-cycle and the off-cycle comprise one of the following pairs: (1) the on-cycle is approximately 8 hours and the off-cycle is approximately 16 hours, (2) the on-cycle is approximately 30 minutes and the off-cycle is approximately 30 minutes, or (3) the on-cycle is approximately 1.5 hours and the off-cycle is approximately 1.5 hours.

22. The computer-readable storage medium of claim 20, wherein the stimulation intensity of the subsensory electrical stimulation is less than or equal to 50% of the stimulation intensity at the sensory threshold.

23. The computer-readable storage medium of claim 20, further comprising instructions that cause the one or more processors to:
during the therapy maintenance phase, revert to continuous delivery of the sensory electrical stimulation at the sensory threshold to the patient based on the first set of therapy parameters in response to a patient request.

\* \* \* \* \*